United States Patent
Boyle et al.

(10) Patent No.: US 12,390,509 B2
(45) Date of Patent: Aug. 19, 2025

(54) PHARMACEUTICAL COMPOSITION COMPRISING FRATAXIN FUSION PROTEIN AND METHODS OF USE THEREOF

(71) Applicant: Larimar Therapeutics, Inc., Bala Cynwyd, PA (US)

(72) Inventors: Denis Boyle, Hermann, MO (US); Thomas Ransohoff, Lexington, MA (US)

(73) Assignee: Larimar Therapeutics, Inc., Bala Cynwyd, PA (US)

( * ) Notice: Subject to any disclaimer, the term of this patent is extended or adjusted under 35 U.S.C. 154(b) by 0 days.

(21) Appl. No.: 17/549,770

(22) Filed: Dec. 13, 2021

(65) Prior Publication Data

US 2022/0193190 A1   Jun. 23, 2022

Related U.S. Application Data

(60) Provisional application No. 63/124,801, filed on Dec. 12, 2020.

(51) Int. Cl.
| | |
|---|---|
| *A61K 38/17* | (2006.01) |
| *A61P 21/00* | (2006.01) |
| *A61P 25/00* | (2006.01) |
| *C07K 14/47* | (2006.01) |

(52) U.S. Cl.
CPC .......... *A61K 38/1709* (2013.01); *A61P 21/00* (2018.01); *A61P 25/00* (2018.01); *C07K 14/47* (2013.01); *C07K 2319/10* (2013.01)

(58) Field of Classification Search
CPC . A61K 38/1709; C07K 14/47; C07K 2319/10
See application file for complete search history.

(56) References Cited

U.S. PATENT DOCUMENTS

| | | |
|---|---|---|
| 11,459,363 B2 | 10/2022 | Payne |
| 2014/0308262 A1 | 10/2014 | Lorberboum-Galski |
| 2016/0060605 A1 | 3/2016 | Testi |
| 2017/0327847 A1 | 11/2017 | Ghadessy et al. |
| 2020/0377951 A1 | 12/2020 | Bettoun |
| 2021/0047378 A1 | 2/2021 | Payne |
| 2021/0156874 A1 | 5/2021 | Bettoun |
| 2021/0355177 A1 | 11/2021 | Bettoun et al. |
| 2021/0363205 A1 | 11/2021 | Bettoun |
| 2022/0276258 A1 | 9/2022 | Bettoun et al. |

FOREIGN PATENT DOCUMENTS

| | | | | |
|---|---|---|---|---|
| AU | 2003279903 A1 | * | 5/2004 | ........... A61K 47/183 |
| CA | 2649538 | * | 11/2007 | |
| EP | 1752536 A1 | | 2/2007 | |
| EP | 2750686 A1 | | 7/2014 | |
| WO | 2005/116204 A1 | | 12/2005 | |
| WO | 2006/108581 A2 | | 10/2006 | |
| WO | WO 2007/124082 | * | 11/2007 | |
| WO | 2011/103536 A1 | | 8/2011 | |
| WO | 2012/174452 A1 | | 12/2012 | |
| WO | 2013/036596 A2 | | 3/2013 | |
| WO | 2013/071440 A1 | | 5/2013 | |
| WO | 2016/172659 A1 | | 10/2016 | |
| WO | 2017/161354 A1 | | 9/2017 | |
| WO | 2021/011929 A1 | | 1/2021 | |
| WO | 2021/021931 A1 | | 2/2021 | |

OTHER PUBLICATIONS

AU2003279903, Text format, Year 2003.*
European Medicines Agency, Public summary of opinion on orphan designation: Human Frataxin fused to TAT cell-penetrating peptide for the treatment of Friedreich's ataxia. Nov. 13, 2020. One page.
Khdour et al., Lipophilic methylene blue analogues enhance mitochondrial function and increase frataxin levels in a cellular model of Friedreich's ataxia. Bioorg Med Chem. Jul. 23, 2018;26(12):3359-3369.
Pandolfo, Drug Insight: antioxidant therapy in inherited ataxias. Nat Clin Pract Neurol. Feb. 2008;4(2):86-96.
Schultz et al., Off-target effects dominate a large-scale RNAi screen for modulators of the TGF-ß pathway and reveal microRNA regulation of TGFBR2. Silence. Mar. 14, 2011;2:3, 20 pages.
Shoichet et al., Frataxin promotes antioxidant defense in a thiol-dependent manner resulting in diminished malignant transformation in vitro. Hum Mol Genet. Apr. 1, 2002;11(7):815-21.
Vyas et al., A TAT-frataxin fusion protein increases lifespan and cardiac function in a conditional Friedreich's ataxia mouse model. Hum Mol Genet. Mar. 15, 2012;21(6):1230-47.
International Search Report and Written Opinion for Application No. PCT/US2020/044069, dated Oct. 28, 2020, 12 pages.
International Search Report and Written Opinion for Application No. PCT/US2020/044400, dated Oct. 22, 2020, 19 pages.
International Search Report and Written Opinion for Application No. PCT/US2020/062355, dated Mar. 12, 2021, 13 pages.
International Search Report and Written Opinion for Application No. PCT/US2021/063163, dated Apr. 11, 2022, 16 pages.

* cited by examiner

*Primary Examiner* — Gyan Chandra
(74) *Attorney, Agent, or Firm* — McCarter & English, LLP; Jill Mello; Yelena Margolin

(57) ABSTRACT

Pharmaceutical compositions comprising a TAT-FXN fusion polypeptide are disclosed, as are methods of use of the pharmaceutical compositions to treat subjects diagnosed with Friedrich's Ataxia and/or hypertrophic cardiomyopathy.

56 Claims, 2 Drawing Sheets
Specification includes a Sequence Listing.

PHARMACEUTICAL COMPOSITION COMPRISING FRATAXIN FUSION PROTEIN AND METHODS OF USE THEREOF

RELATED APPLICATIONS

This application claims priority to U.S. Provisional Application No. 63/124,801, filed on Dec. 12, 2020, the entire contents of which are hereby incorporated herein by reference.

SEQUENCE LISTING

The instant application contains a Sequence Listing which has been submitted electronically in ASCII format and is hereby incorporated by reference in its entirety. Said ASCII copy, created on Dec. 10, 2021, is named 130197-01202_SL.txt and is 8,312 bytes in size.

BACKGROUND

Friedreich's Ataxia (FRDA) is a rare genetic, progressive neurodegenerative disorder caused by a mutation in a gene encoding frataxin (FXN). FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form. In humans, the 210-amino acid full-length hFXN (hFXN1-210, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN81-210).

An FXN fusion protein is currently being developed as an FXN replacement therapy to restore functional levels of FXN in the mitochondria of FRDA patients. The FXN fusion protein has an amino acid sequence of SEQ ID NO: 1 and includes the HIV-TAT peptide linked to the N-terminus of the full-length hFXN protein. The mechanism of action of the FXN fusion protein relies on the cell-penetrating ability of the HIV-TAT peptide to deliver the FXN fusion protein into cells and the subsequent processing into mature hFXN after translocation into the mitochondria. The FXN fusion protein is described in U.S. patent application Ser. No. 16/942,276, the entire contents of each of which are hereby incorporated herein by reference. To facilitate development of the FXN fusion protein of SEQ ID NO: 1 for therapeutic use, pharmaceutical compositions comprising the FXN fusion protein are needed.

SUMMARY OF THE INVENTION

Accordingly, in one aspect, the present disclosure provides a pharmaceutical composition comprising a fusion polypeptide, a pharmaceutically acceptable excipient and a pharmaceutically acceptable carrier, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In one embodiment, the pharmaceutical composition is stable for at least 1 month.

In one embodiment, the pharmaceutical composition is stable for at least 1 month at a temperature selected from the group consisting of: about −60° C. or lower; about −25° C. to about −15° C., about 2° C. to about 8° C.; and about 20° C. to about 30° C.

In one embodiment, said fusion polypeptide comprises an amino acid sequence with at least about 95% sequence identity to the amino acid sequence of SEQ ID NO: 1. In one embodiment, said fusion polypeptide comprises an amino acid sequence with at least about 99% sequence identity to the amino acid sequence of SEQ ID NO: 1. In one embodiment, said fusion polypeptide comprises an amino acid sequence of SEQ ID NO: 1. In one embodiment, said fusion polypeptide consists of an amino acid sequence of SEQ ID NO: 1.

In one embodiment, said fusion polypeptide is present in said composition at a concentration of about 15 mg/mL to about 50 mg/mL, about 20 mg/mL to about 75 mg/mL or about 25 mg/mL to about 100 mg/mL. In one embodiment, said fusion polypeptide is present in said pharmaceutical composition at a concentration of greater than about 15 mg/mL, greater than about 20 mg/mL, greater than about 25 mg/mL, greater than about 30 mg/mL, greater than about 35 mg/mL, greater than about 40 mg/mL, greater than about 45 mg/mL, greater than about 50 mg/mL, greater than about 55 mg/mL, greater than about 60 mg/mL, greater than about 65 mg/mL, greater than about 70 mg/mL, greater than about 75 mg/mL, greater than about 80 mg/mL, greater than about 85 mg/mL, greater than about 90 mg/mL, greater than about 95 mg/mL or greater than about 100 mg/mL. In one embodiment, said fusion polypeptide is present in said pharmaceutical composition at a concentration of about 15 mg/mL or greater, about 20 mg/mL or greater, about 25 mg/mL or greater, about 30 mg/mL or greater, about 35 mg/mL or greater, about 40 mg/mL or greater, about 45 mg/mL or greater, about 50 mg/mL or greater, about 55 mg/mL or greater, about 60 mg/mL or greater, about 65 mg/mL or greater, about 70 mg/mL or greater, about 75 mg/mL or greater, about 80 mg/mL or greater, about 85 mg/mL or greater, about 90 mg/mL or greater, about 95 mg/mL, or greater or about 100 mg/mL or greater.

In one embodiment, said fusion polypeptide is present in said pharmaceutical composition at a concentration of between about 25 mg/mL to about 150 mg/mL. In one embodiment, said fusion polypeptide is present in said pharmaceutical composition at a concentration of about 50 mg/mL. In one embodiment, said fusion polypeptide is present is said pharmaceutical composition at a concentration of about 100 mg/mL.

In one embodiment, the pharmaceutically acceptable excipient is selected from the group consisting of a salt, a sugar, an amino acid, or a combination thereof.

In one embodiment, the pharmaceutically acceptable excipient is a salt. In one embodiment, the salt is selected from the group consisting of sodium chloride (NaCl) and calcium chloride ($CaCl_2$).

In one embodiment, the pharmaceutically acceptable excipient is an amino acid. In one embodiment, the amino acid is selected from the group consisting of arginine and proline.

In one embodiment, the pharmaceutically acceptable excipient is a sugar. In one embodiment, the sugar is selected from the group consisting of sucrose and mannitol. In one embodiment, the sugar is sucrose. In one embodiment, the sugar is mannitol. In one embodiment, the sugar is present in said pharmaceutical composition at a concentration of about 1 mM to about 500 mM. In one embodiment, the sugar is present in said pharmaceutical composition at a concentration of about 1 mM to about 50 mM, about 25 mM to about 150 mM, about 100 mM to about 300 mM, about 200 mM to about 450 mM, or about 250 mM to about 500 mM. In one embodiment, the sugar is present in said pharmaceutical composition at a concentration of about 250 mM.

In one embodiment, the pharmaceutical composition further comprises a buffer. In one embodiment, said buffer is selected from the group consisting of acetate, succinate, citrate, histidine, phosphate and Tris. In one embodiment, said buffer is selected from the group consisting of acetate, histidine and Tris. In one embodiment, said buffer is histidine.

In one embodiment, said buffer is present in said pharmaceutical composition at a concentration of between about 5 mM to about 500 mM. In one embodiment, said buffer is present in said pharmaceutical composition at a concentration of about 5 mM to about 50 mM, about 25 mM to about 150 mM, about 50 mM to about 250 mM or about 100 mM to about 500 mM. In one embodiment, said buffer is present in said pharmaceutical composition at a concentration of about 20 mM. In one embodiment, the pH of the pharmaceutical composition is between about 4.0 and about 8.5. In one embodiment, the pH of the pharmaceutical composition is between about 5.0 and about 7.0. In one embodiment, the pH of the pharmaceutical composition is about 5.8.

In one embodiment, the pharmaceutical composition further comprises a surfactant. In one embodiment, said surfactant is a non-ionic surfactant. In one embodiment, said surfactant is selected from the group consisting of polyoxyethylene glycol octylphenol ethers (Triton-X 100), polyoxyethylene glycol alkylphenol ethers (Nonoxynol-9), polyoxyethylene glycol sorbitan alkyl esters (Polysorbate), sorbitan alkyl esters (Span), and block copolymers of polyethylene glycol and polypropylene glycol (Poloxamers). In one embodiment, said surfactant is polyethylene glycol sorbitan monolaurate (Polysorbate 20). In one embodiment, said surfactant is present in said pharmaceutical composition at a concentration of about 0.0001% w/v to about 1% w/v. In one embodiment, said surfactant is present in said pharmaceutical composition at a concentration of about 0.0001% w/v to about 0.1% w/v, about 0.01% w/v to about 0.5% w/v, about 0.05% w/v to about 1% w/v, about 0.01% w/v to about 0.1% w/v, about 0.005% w/v to about 0.5% w/v, or about 0.001% w/v to about 1.0% w/v. In one embodiment, said surfactant is present is said pharmaceutical composition at a concentration of about 0.05% w/v.

In one embodiment, said a pharmaceutically acceptable carrier is water.

In another aspect, the disclosure provides a pharmaceutical composition comprising a fusion polypeptide, a pharmaceutically acceptable excipient, a pharmaceutically acceptable carrier, a buffer and a surfactant, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In one embodiment, said pharmaceutically acceptable excipient is sucrose. In one embodiment, said buffer is histidine. In one embodiment, said surfactant is polyethylene glycol sorbitan monolaurate (Polysorbate 20). In one embodiment, said a pharmaceutically acceptable carrier is water.

In yet another aspect, the disclosure provides a pharmaceutical composition comprising a fusion polypeptide, sucrose, histidine, a polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In still another aspect, the disclosure provides a pharmaceutical composition comprising a fusion polypeptide, 250 mM sucrose, 20 mM histidine, 0.05% w/v polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In yet another aspect, the disclosure provides a pharmaceutical composition comprising a fusion polypeptide, mannitol, histidine, a polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In another aspect, the disclosure provides a pharmaceutical composition comprising a fusion polypeptide, 250 mM mannitol, 20 mM histidine, 0.05% w/v polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL.

In another aspect, the present disclosure provides a pharmaceutical composition comprising a fusion polypeptide, 250 mM sucrose, 20 mM histidine, 0.05% w/v polyethylene glycol sorbitan monolaurate (Polysorbate 20) and water, wherein the fusion polypeptide consists of an amino acid sequence of SEQ ID NO: 1; and wherein the fusion polypeptide is present in said composition at a concentration of about 50 mg/mL.

In another aspect, the present disclosure provides a pharmaceutical composition comprising a fusion polypeptide, 250 mM mannitol, 20 mM histidine, 0.05% w/v polyethylene glycol sorbitan monolaurate (Polysorbate 20) and water, wherein the fusion polypeptide consists of an amino acid sequence of SEQ ID NO: 1; and wherein the fusion polypeptide is present in said composition at a concentration of about 50 mg/mL.

In one embodiment, said pharmaceutical composition exhibits stability. In one embodiment, said pharmaceutical composition is in a lyophilized form. In one embodiment, said pharmaceutical composition is suitable for injection.

In some embodiments, the pharmaceutical composition is in liquid form and stable when stored at the temperature of about −60° C. or lower for at least about 1 month, at least 2 months, at least 3 months, at least 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months.

In some embodiments, the pharmaceutical composition is in liquid form and stable when stored at the temperature of about −25° C. to about −15° C. for at least about 1 month, at least 2 months, at least 3 months, at least 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months.

In some embodiments, the pharmaceutical composition is in lyophilized form and stable when stored at the temperature of about 2° C. to about 8° C. for at least about 1 month, at least 2 months, at least 3 months, at least 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months.

In some embodiments, the pharmaceutical composition is in lyophilized form and stable when stored at the temperature of about 20° C. to about 30° C. for at least about 1 month, at least 2 months, at least 3 months, at least 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, or at least about 18 months.

In one embodiment, said pharmaceutical composition is suitable for a subcutaneous injection.

In another aspect, the invention provides a method of treating or preventing a disease, said method comprising administering to a subject in need thereof a pharmaceutical composition of the present disclosure, such that said disease in said subject is treated or prevented. In one embodiment, said disease is Friedreich's Ataxia (FRDA). In one embodiment, said disease is an FRDA-associated disease.

Figure 1:
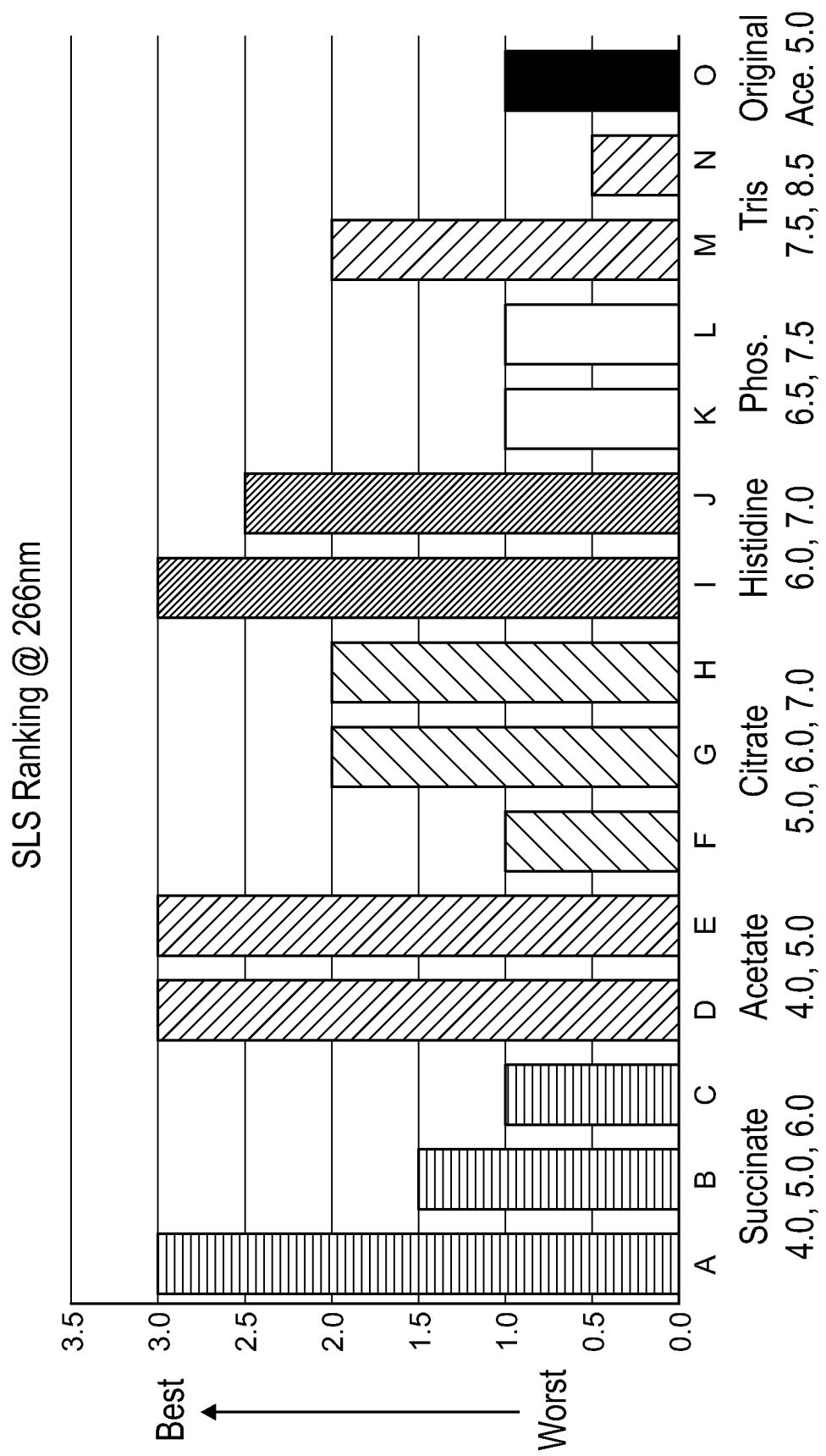
FIG. 1 is a bar graph showing $T_{agg}$ at 266 nm formulation ranking results.

```
SEQUENCES OF THE DISCLOSURE
SEQ ID NO: 1,
Amino acid sequence of a TAT-FXN fusion
polypeptide (224 AA):
MYGRKKRRQR RRGGMWTLGR RAVAGLLASP

SPAQAQTLTR VPRPAELAPL CGRRGLRTDI

DATCTPRRAS SNQRGLNQIW NVKKQSVYLM

NLRKSGTLGH PGSLDETTYE RLAEETLDSL

AEFFEDLADK PYTFEDYDVS FGSGVLTVKL
```

```
-continued
GGDLGTYVIN KQTPNKQIWL SSPSSGPKRY

DWTGKNWVYS HDGVSLHELL AAELTKALKT

KLDLS SLAYS GKDA.

SEQ ID NO: 2,
Complete amino acid sequence of the HIV-1
transactivator of transcription cell
penetrating peptide (TAT-cpp), with a
methionine added at the amino terminus
for initiation (12 AA):
MYGRKKRRQRRR SEQ ID NO: 3, Amino acid sequence of the
mitochondrial targeting sequence of human
frataxin (hFXN-mts) (80 AA):
MWTLGR RAVAGLLASP SPAQAQTLTR VPRPAELAPL

CGRRGLRTDI DATCTPRRAS SNQRGLNQIW

NVKKQSVYLM NLRK

SEQ ID NO: 4,
Amino acid sequence of complete human
Frataxin protein (hFXN) (210 AA):
MWTLGR RAVAGLLASP SPAQAQTLTR VPRPAELAPL

CGRRGLRTDI DATCTPRRAS SNQRGLNQIW

NVKKQSVYLM NLRKSGTLGH PGSLDETTYE

RLAEETLDSL AEFFEDLADK PYTFEDYDVS

FGSGVLTVKL GGDLGTYVIN KQTPNKQIWL

SSPSSGPKRY DWTGKNWVYS HDGVSLHELL

AAELTKALKT KLDLSSLAYS GKDA

SEQ ID NO: 5,
Amino acid sequence of mature human
Frataxin protein (130 AA):
SGTLGH PGSLDETTYE RLAEETLDSL

AEFFEDLADK PYTFEDYDVS FGSGVLTVKL

GGDLGTYVIN KQTPNKQIWL SSPSSGPKRY

DWTGKNWVYS HDGVSLHELL AAELTKALKT

KLDLS SLAYS GKDA

SEQ ID NO: 6, Nucleic acid sequence (cDNA)
encoding the TAT-FXN fusion polypeptide of
SEQ ID NO: 1; optimized for expression in
E. coli (684 bases):
CATATGTATGGTAGAAAGAAACGTCGTCAACGTCGTCG

TGGTGGTATGTGGACCTTGGGCCGTCGCGCGGTTGCGG

GCCTGCTGGCGAGCCCAAGCCCGGCACAGGCGCAGACC

CTGACGCGCGTTCCGCGTCCGGCGGAATTGGCCCCGTT

GTGCGGTCGCCGTGGTCTGCGCACGGATATCGACGCTA

CCTGTACGCCGCGTCGCGCGAGCAGCAATCAGCGTGGC

CTGAATCAAATTTGGAACGTCAAGAAACAATCTGTTTA

CCTGATGAATCTGCGCAAGAGCGGTACGTTGGGTCACC

CGGGCAGCCTGGACGAGACTACCTATGAGCGCCTGGCT

GAGGAAACGCTGGACAGCCTGGCCGAATTTTTCGAAGA

TCTCGCAGATAAGCCGTACACGTTTGAGGATTATGACG

TGAGCTTCGGCAGCGGCGTCTTAACCGTGAAACTGGGT
```

-continued

```
GGTGACCTGGGCACCTACGTGATCAATAAGCAAACCCC

GAACAAACAGATTTGGCTGAGCTCGCCGAGCTCTGGCC

CTAAGCGTTACGATTGGACCGGTAAGAACTGGGTGTAT

TCCCACGACGGTGTCAGCCTGCATGAACTGCTGGCGGC

AGAGCTGACCAAAGCGCTGAAAACTAAACTGGATCTGA

GCTCCCTGGCCTACAGCGGTAAAGACGCATAACTCGAG

SEQ ID NO: 7:
complete amino acid sequence of the HIV-1
transactivator of transcription cell
penetrating peptide (TAT-cpp) (11 AA):
YGRKKRRQRRR.
```

DETAILED DESCRIPTION OF THE INVENTION

For the purposes of promoting an understanding of the principles of the novel technology, reference will now be made to the preferred compositions, methods of making, and methods of use thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Definitions

Unless otherwise indicated in the context a term is used, the terms will have the following meanings as utilized herein.

The term "about" refers to a range of values plus or minus 10 percent, e.g., about 1.0 encompasses values from 0.9 to 1.1.

"Pharmaceutically acceptable" refers to approved or approvable by a regulatory agency of a government, such as the U.S. Food and Drug Administration (U.S. FDA) or the European EMA, or listed in the U.S. Pharmacopoeia or other generally recognized pharmacopoeia for use in mammals and/or animals, and more particularly in humans.

A "subject" as used herein refers to a mammal, e.g., a monkey, a rat, a mouse, or a human. In one specific embodiment, a subject is a human.

"Treat," "treating" or "treatment" of any disease refers to reversing, alleviating, arresting, or ameliorating a disease or at least one of the clinical symptoms of a disease or inhibiting the progress of a disease or at least one of the clinical symptoms of the disease, in this case Friedreich's Ataxia (FRDA). "Treat," "treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject.

"Therapeutically effective amount" refers to the amount of an active pharmaceutical ingredient that, when administered to a subject for treating a disease, or at least one of the clinical symptoms of a disease, is sufficient to affect such treatment of the disease or symptom thereof. The "therapeutically effective amount" may vary depending, for example, on the active pharmaceutical ingredient, the disease and/or symptoms of the disease, severity of the disease and/or symptoms of the disease or disorder, the age, weight, and/or health of the subject to be treated, and the judgment of the prescribing physician.

For example, a "therapeutically effective amount" of the disclosed TAT-FXN fusion polypeptide is that amount which is necessary or sufficient to treat FRDA, including, e.g., an FRDA-associated disease, disorder or condition. For example, a "therapeutically effective amount" of the disclosed TAT-FXN fusion polypeptide is that amount which is necessary or sufficient to ameliorate, improve or achieve a reduction in the severity of at least one symptom or indicator associated with FRDA, or to delay progression of FRDA, including, e.g., an FRDA-associated disease, disorder or condition. In some embodiments, the term "therapeutically effective amount" of the disclosed TAT-FXN fusion polypeptide may also be that amount which is necessary or sufficient to cause an increase the amount of hFXN in at least one tissue of a subject who is being administered the TAT-FXN fusion polypeptide.

"Therapeutically effective dose" refers to a dose that provides effective treatment of a disease or disorder in a subject. A therapeutically effective dose may vary from active pharmaceutical ingredient to active pharmaceutical ingredient, and from subject to subject, and may depend upon factors such as the condition of the subject, genetic character of the subject, and the route of delivery.

Friedreich's Ataxia and FXN

In spite of its rarity, Friedreich's Ataxia (FRDA) is the most common inherited ataxia in humans, with an estimated 4,000-5,000 cases in the United States. FRDA is thought to result from a deficiency of the mitochondrial protein frataxin (FXN), and specifically human frataxin (hFXN). The FXN protein is an essential and phylogenetically conserved protein that is found in cells throughout the body. The highest levels of FXN are found in the heart, spinal cord, liver, pancreas, and skeletal muscle. FXN is encoded in the nucleus, expressed in the cytoplasm and imported into the mitochondria where it is processed to its mature form. In humans, the 210-amino acid full-length hFXN (23.1 kDa) contains a typical mitochondrial targeting sequence (MTS) at the amino terminus that is processed in a 2-step cleavage by the mitochondrial processing peptidase (MPP) as it is imported into the mitochondrial matrix. The resulting protein is a 130-amino acid, 14.2 kDa mature hFXN protein. There have been no other intra-mitochondrial post-translational modifications identified.

The exact function of FXN has not been defined. Published literature and research indicate FXN could play several roles in mitochondrial iron homeostasis, notably in the de novo biosynthesis of iron-sulfur (Fe—S) cluster proteins, by presenting iron to Fe—S cluster assembly enzyme scaffold proteins, and heme synthesis. In the absence of FXN, free iron can accumulate in mitochondria with loss of activity of Fe—S cluster containing proteins. Important and key Fe—S cluster dependent enzyme systems include Complexes I, II, and III of the electron transport chain, and aconitase of the Krebs Cycle.

FRDA generally manifests as a progressive multisystem disease, typically beginning in mid-childhood. Patients suffer from multiple symptoms, including progressive neurologic and cardiac dysfunction. Key among these is a primary neurodegeneration of the dorsal root ganglia and the dentate nucleus of the cerebellum leading to the hallmark clinical findings of progressive limb ataxia and dysarthria. Hypertrophic cardiomyopathy is also common and is associated with early mortality in the 3rd to 5th decade of life in FRDA subjects. Other clinical findings can include scoliosis, fatigue, diabetes, visual impairment, and hearing loss.

Inheritance associated with FRDA is autosomal recessive and is predominantly caused by an inherited GAA triplet expansion in the first intron of both alleles of the hFXN gene. This triplet expansion causes transcriptional repression of the FRDA gene, which causes patients to produce only small quantities of hFXN. Heterozygotes (carriers) typically have hFXN levels at ~50% of normal but are phenotypically normal.

Currently, there are no FDA-approved treatments which directly address or ameliorate the FXN deficiency that occurs with FRDA. Accordingly, the present disclosure provides a pharmaceutical composition comprising a TAT-FXN fusion protein useful for treating FRDA.

TAT-FXN Fusion Polypeptides

In some embodiments, the present disclosure provides a pharmaceutical composition comprising a TAT-FXN fusion polypeptide as disclosed herein. For example, a TAT-FXN fusion polypeptide can be a polypeptide that comprises an amino acid sequence with at least about 90% sequence identity to human frataxin (FXN, SEQ ID NO: 4; or mature FXN, SEQ ID NO: 5), fused to an amino acid sequence with at least about 90% sequence identity to TAT-CPP (cell penetrant peptide, SEQ ID NO: 2 or SEQ ID NO: 7) as disclosed herein.

Frataxin (e.g., complete human frataxin protein, SEQ ID NO: 4) is an essential and highly conserved protein expressed in most eukaryotic organisms and targeted to the mitochondrial matrix. It appears to function in mitochondrial iron homeostasis, notably in the de novo biosynthesis of iron-sulfur (Fe—S) cluster proteins, by presenting iron to IscU scaffold proteins, and heme. Iron-sulfur clusters are integral and essential components of multiple protein complexes in mitochondria, including Complexes I, II, and III of the electron transport chain, as well as aconitase and succinate dehydrogenase of the Krebs Cycle. Iron-Sulfur clusters are also used extensively throughout the cytosol and nucleus of the cell. In its absence, free iron accumulates in mitochondria with loss of activity of Fe—S containing proteins, and loss of energy production due to electron transport chain damage and extensive mitochondrial protein acetylation.

In some embodiments, the TAT-FXN fusion polypeptide comprised in the pharmaceutical compositions of the present disclosure may comprise an amino acid sequence with at least about 90% sequence identity, e.g., about 95%, about 96%, about 97%, about 98%, about 99% or about 100% sequence identity, to the amino acid sequence of the complete human frataxin protein (SEQ ID NO: 4). In some embodiments, the TAT-FXN fusion polypeptide disclosed herein may comprise an amino acid sequence with at least about 90% sequence identity, e.g., about 95%, about 96%, about 97%, about 98%, about 99% or about 100% sequence identity, to the amino acid sequence of the mature human frataxin protein (SEQ ID NO: 5).

In some embodiments, the TAT-FXN fusion polypeptide comprised in the pharmaceutical compositions of the present disclosure may comprise at least one (e.g., 2, 3, 4, 5, 6, 7, 8, 9, 10 or more) point mutation in the amino acid sequence of the complete human frataxin protein (SEQ ID NO: 4) or the amino acid sequence of the mature human frataxin protein (SEQ ID NO: 5). Examples of point mutations that may be comprised in frataxin are described, e.g., in U.S. Pat. No. 9,217,019, the entire contents of which are hereby incorporated herein by reference. In one specific embodiment, a TAT-FXN fusion polypeptide may comprise a mutation at the amino acid position 147 of SEQ ID NO: 4 or position 67 of SEQ ID NO: 5. For example, the lysine (K) residue at amino acid position 147 of SEQ ID NO: 4 or at amino acid position 67 of SEQ ID NO: 5 may be substituted with a different amino acid residue, such as a histidine, serine, threonine, asparagine, glutamine, glycine, alanine, valine, isoleucine, leucine, methionine, phenylalanine, tyrosine, tryptophan, cysteine, proline, aspartic acid, or glutamic acid residue. In one embodiment, the lysine (K) residue at amino acid position 147 of SEQ ID NO: 4 or at amino acid position 67 of SEQ ID NO: 5 may be substituted with an arginine (R) residue.

TAT-CPP (cell penetrant peptide, e.g., SEQ ID NO: 2 or SEQ ID NO: 7) is a short, cationic peptide derived from the larger TAT protein of HIV that has cell penetrant properties. TAT has been used to transduce multiple cargos, such as proteins, into cells and tissues in animals. Cell penetrant peptides can transport a variety of molecules, such as proteins, peptides, or oligonucleotides into cells which otherwise cannot absorb large molecular weight compounds. Delivery of a cargo by a cell penetrant peptide has been accomplished for multiple organelles, such as mitochondria, lysosomes, and the nucleus, and they are capable of delivering a cargo across the placenta. TAT has already been used to replace missing cytosolic enzymes in animal models of disease, such as purine nucleoside phosphorylase and in animal models of human mitochondrial diseases, such as lipoamide dehydrogenase deficiency and Friedreich's Ataxia.

Without wishing to be bound by any theory, it is presently believed that the TAT-CPP peptide of SEQ ID NO: 2 or SEQ ID NO: 7 serves to deliver a TAT-FXN fusion polypeptide across cell membranes into mitochondria. The mitochondria can then properly process the TAT-FXN fusion polypeptide via proteolytic processing to remove the transit peptide sequences TAT-CPP (SEQ ID NO: 2 or SEQ ID NO: 7) and MTS (SEQ ID NO: 3), releasing mature FXN (the C-terminal 130 amino acids of the hFXN protein; SEQ ID NO: 5) and other possible active degradant(s) into the mitochondria.

In some embodiments, the TAT-FXN fusion polypeptide comprised in the pharmaceutical compositions of the present disclosure can comprise or consist of a peptide having the amino acid sequence of SEQ ID NO: 1. The TAT-FXN fusion polypeptide can therefore be a 224-amino acid recombinant fusion polypeptide comprising a short, cationic cell penetrating peptide, TAT-CPP (SEQ ID NO: 2), fused through a di-peptide (Gly-Gly) linker to the amino-terminus of the complete human frataxin protein (hFXN) (SEQ ID NO: 4), which includes the native mitochondrial targeting sequence (MTS) (SEQ ID NO: 3) of hFXN. Put another way, the disclosed TAT-FXN fusion polypeptide can be a 224-amino acid recombinant fusion polypeptide comprising a short, cationic cell penetrating peptide, TAT-CPP (SEQ ID NO: 2), fused through a di-peptide (Gly-Gly) linker to the amino-terminus of the native mitochondrial targeting sequence (MTS) (SEQ ID NO: 3) of hFXN, which is fused to the amino-terminus of the mature human frataxin protein (hFXN) (SEQ ID NO: 5).

In some embodiments, the TAT-FXN fusion polypeptide comprised in the pharmaceutical compositions of the present disclosure, e.g., the fusion polypeptide comprising, or consisting of, SEQ ID NO: 1, has a molecular weight of about 24.92 kDa.

In embodiments, the TAT-FXN fusion polypeptide comprised in the pharmaceutical compositions of the present disclosure has no unnecessary sequences. For example, the TAT-FXN fusion polypeptide of SEQ ID NO: 1 is approximately 40 aa shorter than a TAT-FXN fusion polypeptide disclosed in Vyas et al., *Hum Mol Genet.* 2012, 21(6):1320-1247. The shorter length of the TAT-FXN fusion polypeptide is due, in part, to the short, 2-amino acid Gly-Gly linker present in the TAT-FXN fusion polypeptide. The shorter length of the TAT-FXN fusion polypeptide as compared to the length of the Vyas et al. polypeptide significantly reduces antigenic potential of the TAT-FXN fusion polypeptide to help ensure subjects will not develop a humoral immune response to the TAT-FXN fusion polypeptide with repeated injections. Development of a humoral immune response would decrease the therapeutic efficacy of the TAT-FXN fusion polypeptide. The polypeptide disclosed in Vyas et al. is associated with an increased risk of developing such an immune response due to its larger size; this fact is acknowledged by the authors of Vyas et al. themselves (see Vyas et al., supra, at p. 1242.). The increased risk of antigenicity is due, at least in part, to the length of the Vyas et al. linker.

In contrast, the TAT-FXN fusion polypeptide comprised in the pharmaceutical compositions of the present disclosure contains, in some embodiments, only a 1, 2 or 3-amino acid linker, e.g., a 2-amino acid Gly-Gly linker. This linker was specifically selected to minimize, if not eliminate, the risk of the TAT-FXN fusion polypeptide triggering a humoral immune response after prolonged introduction into a subject.

Although the selected Gly-Gly linker is expected to minimize antigenicity (i.e., reduce the risk of humoral immune response), it will be recognized that, in some embodiments, other short, non-antigenic linkers may be used in place of Gly-Gly to link TAT and FXN peptides. Such alternative linkers are known in the art and are generally rich in small or polar amino acids such as glycine and serine to provide good flexibility and solubility. Examples of alternative linkers include glycine repeat linkers ($(Gly)_n$; e.g., $(Gly)_8$ (SEQ ID NO: 8)) and "GS" linkers primarily made up of stretches of glycine and serine (e.g., $(Gly-Gly-Gly-Gly-Ser)_n$ (SEQ ID NO: 9)), although others are also known (e.g., Gly-Ser-Ala-Gly-Ser-Ala-Ala-Gly-Ser-Gly-Glu-Phe (SEQ ID NO: 10)). An alternative linker to Gly-Gly should remain short (e.g., 20 or fewer amino acids, such as 1, 2 or 3 amino acids). Alternative linkers that minimize antigenicity, result in good fusion polypeptide solubility, and are expressible from a desired expression system are also contemplated by the present disclosure.

In some embodiments, the TAT-FXN fusion polypeptide comprised in the pharmaceutical compositions of the present disclosure can also omit a linker. For example, a TAT-FXN fusion polypeptide may consist of a first peptide having an amino acid sequence with at least about 90% sequence identity, e.g., at least about 95% or about 100% sequence identity, to SEQ ID NO: 2 or SEQ ID NO: 7 and a second peptide having an amino acid sequence with at least about 90% sequence identity, e.g., at least about 95% or about 100% sequence identity, to SEQ ID NO: 4. In another example, the TAT-FXN fusion polypeptide may consist of a first peptide having an amino acid sequence with at least about 90% sequence identity, e.g., at least about 95% or about 100% sequence identity, to SEQ ID NO: 2 or SEQ ID NO: 7; a second peptide having an amino acid sequence with at least about 90% sequence identity, e.g., at least about 95% or about 100% sequence identity, to SEQ ID NO: 3; and a third peptide having an amino acid sequence with at least about 90% sequence identity, e.g., at least about 95% or about 100% sequence identity, to SEQ ID NO: 5.

In some embodiments, a TAT-FXN fusion polypeptide comprised in the pharmaceutical compositions of the present disclosure, e.g., TAT-FXN fusion polypeptide of SEQ ID NO: 1, comprises an FXN polypeptide that has 100% sequence identity with the human FXN protein. A TAT-FXN fusion polypeptide of the present disclosure with an amino acid sequence that is 100% identical to the amino acid sequence of human frataxin is expected to be associated with optimal sequence recognition and processing by the mitochondrial processing peptidase, as well as decreased antigenicity of the TAT-FXN fusion polypeptide.

In some embodiments of the present disclosure, the TAT-FXN fusion polypeptides possess desirable solubility. For example, the TAT-FXN fusion polypeptides, e.g., having the amino acid sequence of SEQ ID NO.1, may possess physical parameters as provided in Table A below.

TABLE A

Physical parameters of TAT-FXN fusion polypeptide

| Parameter | TAT-FXN |
| --- | --- |
| Number of amino acids | 224 |
| Molecular Weight | 24,922.26 |
| Theoretical pI | 9.72 |
| Total number (−) charged aa | 23 |
| Total number (+) charged aa | 34 |
| Estimated half-life | 30 hours |
| Instability Index | 53.51 |
| Aliphatic Index | 76.25 |
| Hydropathicity (GRAVY index) | −0.610 |

The GRAVY (Grand Average of Hydropathy) value for a peptide is calculated as the sum of hydropathy values of all the amino acids, divided by the number of residues in the sequence. The larger the number, the more hydrophobic the peptide.

The aliphatic index is the relative volume occupied by aliphatic side chains (alanine, valine, isoleucine, and leucine). It may be regarded as a positive factor for the increase of thermostability of globular proteins.

The solubility of the TAT-FXN fusion polypeptide comprised in the pharmaceutical compositions of the present disclosure is evidenced by the aliphatic index and hydropathicity index of the TAT-FXN fusion polypeptide. As can be appreciated, improved and maintained solubility allows for greater accuracy in dosing and can dramatically reduce the volume of a therapeutic dose needed to achieve a desired effect.

In some embodiments, the TAT-FXN fusion polypeptide comprised in the pharmaceutical compositions of the present disclosure is soluble in pH buffers at physiologic pH, making it compatible with human subcutaneous injection.

In some embodiments, the TAT-FXN fusion polypeptide comprised in the pharmaceutical compositions of the present disclosure is a TAT-FXN fusion polypeptide described in U.S. Provisional Application No. 62/880,073, U.S. Provisional Application No. 62/891,029, U.S. patent application Ser. No. 16/942,276 and International Patent Application No. PCT/US2020/044069, the entire contents of each of which are hereby incorporated herein by reference.

Pharmaceutical Composition

The present disclosure provides pharmaceutical compositions comprising the TAT-FXN fusion polypeptide described herein, e.g., a fusion polypeptide with at least about 90%, at least about 95%, at least about 99% or 100% sequence identity to amino acid sequence of SEQ ID NO: 1.

In some embodiments, the fusion polypeptide is present in said pharmaceutical composition at a concentration of greater than about 10 mg/mL, e.g., about 15 mg/mL to about 50 mg/mL, about 20 mg/mL to about 75 mg/mL or about 25 mg/mL to about 100 mg/mL. In some embodiments, the fusion polypeptide is present in the pharmaceutical composition at a concentration of greater than about 15 mg/mL, greater than about 20 mg/mL, greater than about 25 mg/mL, greater than about 30 mg/mL, greater than about 35 mg/mL, greater than about 40 mg/mL, greater than about 45 mg/mL, greater than about 50 mg/mL, greater than about 55 mg/mL, greater than about 60 mg/mL, greater than about 65 mg/mL, greater than about 70 mg/mL, greater than about 75 mg/mL, greater than about 80 mg/mL, greater than about 85 mg/mL, greater than about 90 mg/mL, greater than about 95 mg/mL or greater than about 100 mg/mL. In some embodiments, the fusion polypeptide is present in the pharmaceutical composition at a concentration of about 15 mg/mL or greater, about 20 mg/mL or greater, about 25 mg/mL or greater, about 30 mg/mL or greater, about 35 mg/mL or greater, about 40 mg/mL or greater, about 45 mg/mL or greater, about 50 mg/mL or greater, about 55 mg/mL or greater, about 60 mg/mL or greater, about 65 mg/mL or greater, about 70 mg/mL or greater, about 75 mg/mL or greater, about 80 mg/mL or greater, about 85 mg/mL or greater, about 90 mg/mL or greater, about 95 mg/mL or greater, or about 100 mg/mL or greater.

For example, the fusion polypeptide may be present in the pharmaceutical composition at a concentration of between about 25 mg/mL to about 150 mg/mL. In embodiments, the fusion polypeptide is present is said pharmaceutical composition at a concentration of about 10, 15, 20, 25, 30, 35, 40, 45, 50, 55, 60, 65, 70, 75, 80, 85, 90, 95 or 100 mg/mL. In one embodiment, the fusion polypeptide is present in said pharmaceutical composition at a concentration of about 50 mg/mL. In another embodiment, the fusion polypeptide is present is said pharmaceutical composition at a concentration of about 100 mg/mL.

In some examples, the TAT-FXN fusion polypeptide present in the pharmaceutical compositions of the present disclosure retains its thermal and conformational stability. In some examples, the TAT-FXN fusion polypeptide present in the pharmaceutical compositions of the present disclosure does not form insoluble aggregates. Methods for measuring thermal and conformational stability of a protein and aggregation of a protein are known in the art and include, e.g., Differential Scanning Fluorimetry (DSF), Dynamic Light Scattering (DLS) and Static Light Scattering (SLS)

In some embodiments, a pharmaceutical composition of the present disclosure is stable when stored at a temperature of about −60° C. or lower for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months. In some embodiments, the pharmaceutical composition is in a liquid form. In some embodiments, the pharmaceutical composition comprises TAT-FXN fusion polypeptide comprising or consisting of SEQ ID NO: 1 at a concentration of about 50 mg/mL, about 20 mM histidine, about 250 mM sucrose, about 0.05% polysorbate 20 (PS 20), at pH of about 5.8.

In some embodiments, a pharmaceutical composition of the present disclosure is stable when stored at a temperature of about −25° C. to about −15° C., e.g., about −20° C. or −25° C., for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months. In some embodiments, the pharmaceutical composition is in a liquid form. In some embodiments, the pharmaceutical composition comprises TAT-FXN fusion polypeptide comprising or consisting of SEQ ID NO: 1 at a concentration of about 50 mg/mL, about 20 mM histidine, about 250 mM sucrose, about 0.05% polysorbate 20 (PS 20), at pH of about 5.8.

In some embodiments, a pharmaceutical composition of the present disclosure is stable when stored at a temperature of about 2° C. to about 8° C., e.g., about 4° C., for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months or at least about 24 months. In some embodiments, the pharmaceutical composition is in a lyophilized form. In some embodiments, the pharmaceutical composition comprises TAT-FXN fusion polypeptide comprising or consisting of SEQ ID NO: 1 at a concentration of about 50 mg/mL, about 20 mM histidine, about 250 mM sucrose, about 0.05% polysorbate 20 (PS 20), at pH of about 5.8.

In some embodiments, a pharmaceutical composition of the present disclosure is stable when stored at a temperature of about 20° C. to about 30° C., e.g., about 25° C., for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, or at least about 18 months. In some embodiments, the pharmaceutical composition is in a lyophilized form. In some embodiments, the pharmaceutical composition comprises TAT-FXN fusion polypeptide comprising or consisting of SEQ ID NO: 1 at a concentration of about 50 mg/mL, about 20 mM histidine, about 250 mM sucrose, about 0.05% polysorbate 20 (PS 20), at pH of about 5.8.

Stability over time of a pharmaceutical composition of the present disclosure comprising TAT-FXN fusion polypeptide may be evaluated, e.g., using the methods known in the art. For example, stability of a pharmaceutical composition of the present disclosure may be evaluated over time based on one or more (any combination of) of the following criteria:
 a) appearance of the pharmaceutical composition, e.g., whether there is a chance in color or opacity of the composition, or whether there are visible particulates present;
 b) pH of the pharmaceutical composition;
 c) protein concentration in the pharmaceutical composition as measured by A280 over time;

d) protein purity as measured by reverse phase chromatography (RP-HPLC) and capillary electrophoresis (CE);
e) main peak purity and presence of higher order aggregates as measured by Size Exclusion Chromagography (SE-UPLC);
f) specific activity of the protein, as measured, e.g., using methods described, e.g., in US Publication No. 2021/0156874 A1, the entire contents of which are hereby incorporated herein by reference;
g) the amount of endotoxin in the pharmaceutical composition;
h) sterility of the pharmaceutical composition; and
i) particulate matter present in the pharmaceutical composition; and
j) container closure integrity for pharmaceutical composition stored in closed vials.

The pharmaceutically acceptable excipients present in the pharmaceutical composition of the present disclosure may be selected from the group consisting of a salt, a sugar, an amino acid, or any combination thereof.

For example, the pharmaceutically acceptable excipient may be a salt, e.g., selected from the group consisting of sodium chloride (NaCl) and calcium chloride (CaCl$_2$).

In some embodiments, the pharmaceutically acceptable excipient is an amino acid, e.g., arginine or proline.

In some embodiments, the pharmaceutically acceptable excipient is a sugar, e.g., sucrose or mannitol. In one embodiment, the sugar is sucrose. In another embodiment, the sugar is mannitol. The sugar may be present in said pharmaceutical composition at a concentration of about 1 mM to about 500 mM. In one embodiment, the sugar is present in said pharmaceutical composition at a concentration of about 1 mM to about 50 mM, about 25 mM to about 150 mM, about 100 mM to about 300 mM, about 200 mM to about 450 mM, or about 250 mM to about 500 mM. For example, the sugar may be present in said pharmaceutical composition at a concentration of about 250 mM.

In some embodiments, the pharmaceutical composition further comprises a buffer, e.g., acetate, succinate, citrate, histidine, phosphate or a Tris buffer. In one embodiment, the buffer may be selected from the group consisting of acetate, histidine and Tris. In one embodiment, the buffer is histidine.

The buffer may be present in said pharmaceutical composition at a concentration of between about 5 mM to about 500 mM. For example, the buffer may be present in the pharmaceutical composition at a concentration of about 5 mM to about 50 mM, about 25 mM to about 150 mM, about 50 mM to about 250 mM or about 100 mM to about 500 mM. In one embodiment, the buffer (e.g., histidine buffer) may be present in said pharmaceutical composition at a concentration of about 20 mM.

The pH of the pharmaceutical composition of the present invention may be between about 4.0 and about 8.5. For example, the pH of the pharmaceutical composition may be between about 5.0 and about 7.0. In some embodiments, the pH of the pharmaceutical composition may be between about 5.0 and about 6.0, between about 5.5 and about 6.5, between about 6.0 and about 7.0, or between about 5.5 and about 6.0. In some embodiments, the pH of the pharmaceutical composition is about 5.5, about 5.6, about 5.7, about 5.8, about 5.9, about 6.0, about 6.1, about 6.2, about 6.3, about 6.4 or about 6.5. In some embodiments, the pH of the pharmaceutical composition is about 5.8. In some embodiments, the pH of the pharmaceutical composition is about 6.0.

The pharmaceutical composition of the present disclosure may further comprise a surfactant, e.g., a non-ionic surfactant. In some examples, the surfactant may be selected from the group consisting of polyoxyethylene glycol octylphenol ethers (Triton-X 100), polyoxyethylene glycol alkylphenol ethers (Nonoxynol-9), polyoxyethylene glycol sorbitan alkyl esters (Polysorbate), sorbitan alkyl esters (Span), and block copolymers of polyethylene glycol and polypropylene glycol (Poloxamers). In one example, the surfactant may be polyethylene glycol sorbitan monolaurate (Polysorbate 20).

The surfactant may be present in the pharmaceutical composition of the disclosure at a concentration of about 0.0001% w/v to about 1% w/v. For example, the surfactant, e.g., Polysorbate 20, may be present in the pharmaceutical composition at a concentration of about 0.0001% w/v to about 0.1% w/v, about 0.01% w/v to about 0.5% w/v, about 0.01% to about 0.05%, about 0.01% to about 0.1%, about 0.05% to about 0.1%, 0.01% to about 0.1%, about 0.05% w/v to about 1% w/v, about 0.01% w/v to about 0.1% w/v, about 0.005% w/v to about 0.5% w/v, or about 0.001% w/v to about 1.0% w/v. In some embodiments, the surfactant, e.g., Polysorbate 20, may be present is said pharmaceutical composition at a concentration of about 0.01%, about 0.02%, 0.03%, 0.04%, 0.05%, 0.06%, 0.07%, 0.08%, 0.09% or 0.10% w/v. In some embodiments, the surfactant, e.g., Polysorbate 20, may be present is said pharmaceutical composition at a concentration of about 0.05% w/v.

In some examples, the pharmaceutical composition of the present disclosure may comprise a pharmaceutically acceptable carrier that is water.

In some examples, a pharmaceutical composition of the disclosure may comprise, or consist of, a fusion polypeptide, a pharmaceutically acceptable excipient, a pharmaceutically acceptable carrier, a buffer and a surfactant, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL (e.g., about 50 ug/mL).

In some examples, a pharmaceutical composition of the disclosure may comprise, or consist of, a fusion polypeptide, sucrose, histidine, a polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL (e.g., about 50 ug/mL).

In some examples, a pharmaceutical composition of the disclosure may comprise, or consist of, a fusion polypeptide, 250 mM sucrose, 20 mM histidine, 0.05% w/v polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL (e.g., about 50 ug/mL).

In some examples, a pharmaceutical composition of the disclosure may comprise, or consist of, a fusion polypeptide, mannitol, histidine, a polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL (e.g., about 50 ug/mL).

In some examples, a pharmaceutical composition of the disclosure may comprise, or consist of, a fusion polypeptide, 250 mM mannitol, 20 mM histidine, 0.05% w/v polyethylene glycol sorbitan monolaurate (Polysorbate 20) and water, wherein said fusion polypeptide comprises an amino acid sequence with at least about 90% sequence identity to the amino acid sequence of SEQ ID NO: 1; and said fusion polypeptide is present in said composition at a concentration of greater than about 10 mg/mL (e.g., about 50 ug/mL).

In some examples, a pharmaceutical composition of the disclosure may comprise, or consist of, a fusion polypeptide, 250 mM sucrose, 20 mM histidine, 0.05% w/v polyethylene glycol sorbitan monolaurate (Polysorbate 20) and water, wherein the fusion polypeptide consists of an amino acid sequence of SEQ ID NO: 1; and wherein the fusion polypeptide is present in said composition at a concentration of greater than about 10 mg/mL, e.g., about 50 mg/mL.

In some examples, a pharmaceutical composition of the disclosure may comprise, or consist of, a fusion polypeptide, 250 mM mannitol, 20 mM histidine, 0.05% w/v polyethylene glycol sorbitan monolaurate (Polysorbate 20) and water, wherein the fusion polypeptide consists of an amino acid sequence of SEQ ID NO: 1; and wherein the fusion polypeptide is present in said composition at a concentration of greater than about 10 mg/mL, e.g., about 50 mg/mL.

In some examples, the pharmaceutical composition of the disclosure suitable for injection, e.g., a subcutaneous injection.

Therapeutic Uses

The pharmaceutical compositions of the present disclosure, i.e., comprising a TAT-FXN fusion polypeptide, can be administered to a subject to treat any condition associated with a deficiency in FXN. The TAT-FXN fusion polypeptide is a chimeric protein comprising a functional version of the FXN protein linked to the HIV-1 TAT-cpp (cell penetrant peptide). Without wishing to be bound by any theory, one possible mechanism of action of the TAT-FXN fusion polypeptide is to deliver mature FXN, and other possible active degradant(s), to the mitochondria of a subject. Delivery to the mitochondria can occur via the TAT peptide. Once inside the mitochondria, proteolytic processing of the fusion polypeptide will result in the release of mature FXN. In an FXN-deficient subject, provision of mature FXN directly to the mitochondria can supplement, if not completely replace, the deficiency in FXN.

Friedreich's Ataxia

Administration of at least one therapeutically effective dose of a pharmaceutical composition comprising a TAT-FXN fusion polypeptide provided by the present disclosure can be clinically effective to treat Friedreich's ataxia (FRDA).

It is presently anticipated that protein replacement therapy with the TAT-FXN fusion polypeptide will correct the metabolic defect in FRDA and restore adequate cellar function in patients. It is also anticipated that treatment with the TAT-FXN fusion polypeptide will change FRDA from a progressive and deadly disease to a chronic condition that is managed by frequent injections of the fusion polypeptide, much as insulin has changed diabetes into a chronic disease with normal life activities. In older FRDA patients with established disease, it is anticipated that administration of the TAT-FXN fusion polypeptide will halt disease progression. In children diagnosed before onset of FRDA symptoms, it is anticipated that administration of the TAT-FXN fusion polypeptide will result in near complete preservation of tissue function and health.

The gene defect for FRDA was identified in 1996 and there is consensus in the field that lack of FXN protein in mitochondria is the biochemical defect. Multiple investigators have shown that replacement of FXN in deficient patient fibroblasts, and even in yeast with loss of FXN, will rescue the phenotype. Thus, the consensus in the field is that therapies for FRDA must include increasing levels of FXN protein in mitochondria of affected tissues. Although the precise function of FXN has yet to be defined, it is clear that FXN participates in iron-sulfur cluster assembly. In its absence, mitochondrial proteins containing an iron-sulfur cluster (Complexes I, II, and III of the electron transport chain, and aconitase of the Krebs cycle) are severely defective in activity. As a result, those tissues with high dependence on energy production by mitochondria, such as heart and brain, are severely affected and greater than about 60% of patients die from heart failure. As with other mitochondrial diseases, multiple organ systems are also impacted, such as eye, hearing, and pancreas. Thus, clinically relevant target tissues include the heart and brain and can be followed by common clinical testing, such as echocardiography, and neurologic assays such as the Friedreich Ataxia Rating Scale (FARS).

Administration of a pharmaceutical composition comprising the disclosed TAT-FXN fusion polypeptide, can, therefore, be effective as a protein replacement therapy in FXN-deficient subjects diagnosed with FRDA, including, e.g., an FRDA-associated disease, disorder or condition, to treat the FRDA, including, e.g., the FRDA-associated disease, disorder or condition.

The term "FRDA", as used herein, encompasses any disease, disorder or condition associated with a frataxin deficiency. The term "FRDA-associated disease, disorder or condition", as used herein, encompasses a disease, disorder or condition secondary to and/or caused by FRDA, i.e., when present in a subject, it accompanies FRDA and is not present in a subject in the absence of FRDA. Non-limiting examples of an FRDA-associated disease, disorder, or condition, include FRDA-associated pneumonia, FRDA-associated hypertrophic cardiomyopathy and FRDA-associated diabetes. Other non-limiting examples of an FRDA-associated disease, disorder or condition include an FRDA-associated disease, disorder or condition characterized by, without limitation:

(1) a neurological deficiency including, without limitation, one or more of the following: loss of proprioception, loss of reflexes, loss of ability to walk, loss of ability to hold gaze with eyes;

(2) impaired swallowing and/or a progressive loss of the ability to swallow; progressive loss of hearing;

(3) progressive loss of vision due to retinal degeneration from lack of FXN;

(4) progressive loss of speech;

(5) metabolic syndrome including, without limitation, elevated triglycerides, low high-density lipoprotein (HDL) cholesterol, and elevated low-density lipoprotein (LDL) cholesterol;

(6) scoliosis that requires surgery to correct; and/or combinations thereof.

In some embodiments, administration of the pharmaceutical composition comprising the disclosed TAT-FXN fusion polypeptide to a subject, may treat FRDA, including, e.g., an FRDA-associated disease, disorder or condition. "Treating FRDA", as used herein, encompasses ameliorating, improving or achieving a reduction in the severity of FRDA, including, e.g., an FRDA-associated disease, disorder or condition. For example, "treating FRDA" encompasses ameliorating, improving or achieving a reduction in at least one symptom or indicator associated with FRDA. "Treating FRDA", as used herein, also encompasses delaying progression of FRDA, including, e.g., an FRDA-associated disease disorder or condition, e.g., delaying appearance of at least one symptom or indicator associated with FRDA or preventing an increase in the severity of at least one symptom or indicator associated with FRDA, in a subject.

In some embodiments, the term "treating FRDA" also encompasses achieving increased survival (e.g., survival time) of a subject, e.g., a human, with FRDA, including, e.g., an FRDA-associated disease, disorder or condition. For example, treatment of FRDA may result in an increased life expectancy of a subject, e.g., a human, with FRDA, including, e.g., an FRDA-associated disease disorder or condition. In some embodiments, treatment of FRDA in the context of the present disclosure may result in an increased life expectancy of a subject of greater than about 10%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, or greater than about 200% or more, as compared to the average life expectancy of one or more control individuals with similar disease without treatment.

In some embodiments, treatment of FRDA, including, e.g., an FRDA-associated disease, disorder or condition, in the context of the present disclosure may result in an increased life expectancy of a subject by greater than about 6 months, greater than about 8 months, greater than about 10 months, greater than about 12 months, greater than about 2 years, greater than about 4 years, greater than about 6 years, greater than about 8 years, or greater than about 10 years or more, as compared to the average life expectancy of one or more control individuals with similar disease without treatment. In some embodiments, treatment of FRDA, including, e.g., an FRDA-associated disease, disorder or condition in the context of the present disclosure may result in a long-term survival of a subject, e.g., a human, with FRDA, including, e.g., an FRDA-associated disease, disorder or condition. The term "long-term survival", as used herein, refers to a survival time or life expectancy longer than about 40 years, 45 years, 50 years, 55 years, 60 years, or longer.

Clinical assessments known to one of ordinary skill in the art may be used to assess FRDA, including, e.g., an FRDA-associated disease, disorder or condition, to determine the severity of the FRDA and/or to determine the effect of administration to a subject of the disclosed TAT-FXN fusion polypeptide and/or a pharmaceutical composition comprising the disclosed TAT-FXN fusion polypeptide. Examples of methods of clinical assessment of FRDA, including assessments of the severity of FRDA, are described, e.g., in Paap et al., "Standardized Assessment of Hereditary Ataxia Patients in Clinical Studies", *Mov Disord Clin Pract.* 2016, 3(3):230-240 and Patel et al., "Progression of Friedreich ataxia: quantitative characterization over 5 years", *Ann Clin Transl Neurol* 2016, 3(9):684-694, the entire contents of each of which are hereby incorporated herein by reference.

Timed 25-Foot Walk (T25-FW) is a quantitative mobility and leg function performance test that measures the time needed to complete a 25-foot walk. In some embodiments, administration to a subject of the disclosed TAT-FXN fusion polypeptide and/or a pharmaceutical composition comprising the disclosed TAT-FXN fusion polypeptide may result in a decrease in the severity of FRDA as measured, e.g., by the time needed to complete a 25-foot walk. For example, administration to a subject of the disclosed TAT-FXN fusion polypeptide and/or a pharmaceutical composition comprising the disclosed TAT-FXN fusion polypeptide may result in a decrease in the time needed to complete a 25-foot walk, e.g., a decrease of at least about 5%, at least about 10%, at least about 25%, or at least about 50% in the time needed to complete a 25-foot walk, as compared to the time needed to complete a 25-foot walk measured in the subject prior to administration of the disclosed TAT-FXN fusion polypeptide and/or a pharmaceutical composition comprising the disclosed TAT-FXN fusion polypeptide, or as compared to a baseline value. A baseline value may be the time needed to complete a 25-food walk measured prior to administration of the disclosed TAT-FXN fusion polypeptide of the disclosure.

In other embodiments, administration to a subject of the disclosed TAT-FXN fusion polypeptide and/or a pharmaceutical composition comprising the disclosed TAT-FXN fusion polypeptide may delay progression of FRDA in the subject as measured, e.g., by the time needed to complete a 25-foot walk. For example, administration to a subject of the disclosed TAT-FXN fusion polypeptide and/or a pharmaceutical composition comprising the disclosed TAT-FXN fusion polypeptide may result in a substantially similar time needed to complete a 25-foot walk, or a lack of a substantial increase in the time needed to complete a 25-foot walk (e.g., less than a 20%, less than a 10%, or less than a 5% increase in the time needed to complete a 25-foot walk), as compared to the baseline value, i.e., time needed to complete a 25-foot walk measured in the subject prior to administration of the disclosed TAT-FXN fusion polypeptide and/or a pharmaceutical composition comprising the disclosed TAT-FXN fusion polypeptide.

The Modified Friedreich's Ataxia Rating Scale (mFARS) is an examination-based rating scale for assessing the severity of FRDA as described, e.g., in Burk et al., "Monitoring progression in Friedreich ataxia (FRDA): the use of clinical scales", *J of Neurochemistry* 2013, 126(suppl. 1):118-124 and Rummey et al., "Psychometric properties of the Friedreich's Ataxia Rating Scale", *Neurol Genet* 2019, 5:e371, the entire contents of each of which are hereby incorporated herein by reference.

In some embodiments, the mFARS score may comprise at least one of the following subscores: a) a score based on the Functional Disability Rating Scale (FARS-FDS; 0-6 scale; assessment usually made by a neurologist; b) a score based on the Activities of Daily Living Scale (FARS-ADL, 0-36 scale; assessment made by a patient or caregiver); and c) a score based on the Neurological Rating Scale (FARS-neuro) 0-125 scale; assessment made by a neurologist). In some examples, the FARS_ADL score is a FARS rating scale assessing subject ability to complete ADLs (e.g., speech, cutting food, dressing, and personal hygiene), with scores ranging from 0 to 36 points. The respondent may be the subject; a combination of the subject and family; or a family member, spouse or caregiver for those subjects unable to complete the test.

In some embodiments, the score based on the Neurological Rating Scale may include modified scoring of the neurological rating scale involving direct subject participation and targeting specific areas impacted by FRDA, such as bulbar, upper limb, lower limb, and upright stability (mFARS-neuro, 0-99 scale). The mFARS-neuro excludes subscale D (peripheral nervous system) and the first 2 questions of subscale A (bulbar) from the neurological rating scale of the FARS questionnaire.

In some embodiments, the mFARS score may be based on two subscores derived from the full FARS questionnaire: mFARS-neuro as described above and the FARS_ADL as described above.

In some embodiments, administration to a subject of the disclosed pharmaceutical composition comprising the disclosed TAT-FXN fusion polypeptide may result in a decrease in the severity of FRDA as measured, e.g., by an mFARS score, or at least one mFARS subscore as described herein. For example, administration to a subject of the disclosed pharmaceutical composition comprising the disclosed TAT-FXN fusion polypeptide may result in a decrease in an mFARS score or at least one mFARS subscore, as compared to a baseline value, i.e., the mFARS score or the at least one mFARS subscore measured in the subject prior to administration of the disclosed pharmaceutical composition comprising the disclosed TAT-FXN fusion polypeptide.

In other embodiments, administration to a subject of the disclosed pharmaceutical composition comprising the disclosed TAT-FXN fusion polypeptide may delay progression of FRDA in the subject as measured, e.g., by an mFARS score or at least one mFARS subscore as disclosed herein. For example, administration to a subject of the disclosed pharmaceutical composition comprising the disclosed TAT-FXN fusion polypeptide may result in a substantially similar mFARS score or at least one mFARS subscore, or a substantial lack of an increase in an mFARS score or at least one mFARS subscore, as compared to a baseline value, i.e., the mFARS score or the at least one mFARS subscore measured in the subject prior to administration of the disclosed pharmaceutical composition comprising the disclosed TAT-FXN fusion polypeptide, or as compared to a baseline value.

The Nine-Hole Peg Test (9HPT) may be used to measure finger dexterity in subjects with FRDA. In this test, a subject is asked to take pegs from a container, one by one, and place them into the nine holes on the board as quickly as possible. The subject must then remove the pegs from the holes, one by one, and replace them back into the container. Scores are based on the time taken to complete the test activity, recorded in seconds.

In some embodiments, administration to a subject of the disclosed pharmaceutical composition comprising the disclosed TAT-FXN fusion polypeptide may result in a decrease in the severity of FRDA as measured, e.g., by a 9HPT score. For example, administration to a subject of the disclosed pharmaceutical composition comprising the disclosed TAT-FXN fusion polypeptide may result in an decrease in a 9HPT score expressed as time to complete the test activity (e.g., at least an about 5%, 10%, 25%, or 50% decrease in a 9HPT score expressed as time to complete the test activity), as compared to a baseline value, i.e., the 9HPT score measured in the subject prior to administration of the disclosed pharmaceutical composition comprising the disclosed TAT-FXN fusion polypeptide.

In other embodiments, administration to a subject of the disclosed pharmaceutical composition comprising the disclosed TAT-FXN fusion polypeptide may delay progression of FRDA in the subject as measured, e.g., by a 9HPT score. For example, administration to a subject of the disclosed pharmaceutical composition comprising the disclosed TAT-FXN fusion polypeptide may result in a substantially similar 9HPT score, or a lack of a substantial increase in a 9HPT score expressed as time to complete the test activity, as compared to a baseline value, i.e., the 9HPT score measured in the subject prior to administration of the disclosed pharmaceutical composition comprising the disclosed TAT-FXN fusion polypeptide.

In some embodiments, administration to a subject of the disclosed pharmaceutical composition comprising the disclosed TAT-FXN fusion polypeptide results in an increase in the level of hFXN in at least one tissue or biological fluid of the subject, as compared to a baseline level, i.e., the hFXN level in the at least one tissue or biological fluid of the subject prior to administration of the disclosed pharmaceutical composition comprising the disclosed TAT-FXN fusion polypeptide. In some embodiments, the increase in the level of hFXN in the at least one tissue or biological fluid of a subject resulting from administration of the disclosed pharmaceutical composition comprising the disclosed TAT-FXN fusion polypeptide to the subject is sufficient to have a therapeutic effect, i.e., sufficient to treat FRDA in the subject.

In some embodiments, administration of the disclosed pharmaceutical composition comprising the disclosed TAT-FXN fusion polypeptide to a subject with FRDA may result in a level of hFXN in at least one tissue or biological fluid of the subject that is lower than the level of hFXN in the at least one tissue or biological fluid of a subject who does not have FRDA (e.g., a normal, healthy subject), but is still sufficient to have a therapeutic effect, i.e., sufficient to treat FRDA in the subject. For example, after administration of the disclosed pharmaceutical composition comprising the disclosed TAT-FXN fusion polypeptide to a subject with FRDA, the level of hFXN in at least one tissue or a biological fluid of the subject may be about 10% to about 50%, about 20% to about 60%, or about 30% to about 80% of the level of hFXN in the at least one tissue or a biological fluid of a subject who does not have FRDA (e.g., a normal, healthy subject), but the level of hFXN is still sufficient to have a therapeutic effect, i.e., sufficient to treat FRDA in the subject.

In some embodiments, administration to a subject with FRDA of the disclosed pharmaceutical composition comprising the disclosed TAT-FXN fusion polypeptide may result in an increase of at least about 5%, about 10%, about 25%, about 50%, about 100%, about 150%, about 200%, about 300%, about 400%, about 500%, or about 600% in the level of hFXN in at least one tissue or biological fluid of the subject, as compared to the hFXN level in the at least one tissue or biological fluid of the subject prior to administration of the disclosed pharmaceutical composition comprising the disclosed TAT-FXN fusion polypeptide, or as compared to a baseline level.

In some embodiments, administration to a subject with FRDA of the disclosed pharmaceutical composition comprising the disclosed TAT-FXN fusion polypeptide may result in an increase of about 5% to about 30%, about 10% to about 50%, about 25% to about 100%, about 50% to about 150%, about 100% to about 300%, about 50% to about 250%, about 150% to about 500% or about 200% to about 700% in the level of hFXN in at least one tissue or biological fluid of the subject, as compared to the hFXN level in the at least one tissue or biological fluid of the subject prior to administration of the disclosed pharmaceutical composition comprising the disclosed TAT-FXN fusion polypeptide, or as compared to a baseline level. In some embodiments, administration to a subject of the disclosed pharmaceutical composition comprising the disclosed TAT-FXN fusion polypeptide may result in an increase of at least about 2-fold, about 3-fold, about 4-fold, about 5-fold in the level of hFXN in at least one tissue or biological fluid of the subject, as compared to the hFXN level in the at least one tissue or biological fluid of the subject prior to administration of the disclosed pharmaceutical composition comprising the disclosed TAT-FXN fusion polypeptide, or as compared to a baseline level. In some embodiments, administration to a subject of the disclosed pharmaceutical composition comprising the disclosed TAT-FXN fusion polypeptide may result in an increase of between about 2-fold and about 5-fold, or between about 2-fold and about 10-fold, in the level of hFXN in at least one tissue or biological fluid of the subject, as compared to the hFXN level in the at least one tissue or biological fluid of the subject prior to administration of the disclosed pharmaceutical composition comprising the disclosed TAT-FXN fusion polypeptide, or as compared to a baseline level.

In some embodiments, the tissue of a subject in which the level of hFXN may be measured and/or increased may be any tissue that is capable of being biopsied. In some embodiments, the tissue may comprise bronchoalveolar tissue (which may be sampled by, e.g., bronchoalveolar brushing), a mucous membrane (e.g., nasal mucous membrane, which may be sampled by, e.g., nose brushing), a hair follicle, skin tissue, or buccal tissue. In some embodiments, the tissue comprises skin tissue or buccal tissue.

In some embodiments, the biological fluid of a subject in which the level of hFXN may be measured and/or increased may be blood or a component thereof (e.g., serum, plasma, platelets, or any other blood component), urine, or saliva.

FRDA-Associated Pneumonia

Subjects diagnosed with FRDA suffer neurodegeneration of the dorsal root ganglia causing progressive ataxia. This typically leads to the progressive loss of an ability to walk, feed oneself, talk, swallow, and pulmonary aspiration. The event of pulmonary aspiration can lead to pneumonia, frequent hospitalizations, and, eventually, death over a period of 10-15 years from the date of diagnosis.

For many of the reasons set forth above, administration of a disclosed pharmaceutical composition comprising a disclosed TAT-FXN fusion polypeptide, can be effective as a protein replacement therapy in FXN-deficient subjects diagnosed with FRDA to prevent pulmonary aspiration, thereby preventing the pneumonia that follows pulmonary aspiration. Accordingly, the present disclosure provides methods of treating an FRDA-associated pneumonia in a subject, comprising administering to a subject in need thereof a pharmaceutical composition comprising a TAT-FXN fusion polypeptide of the disclosure, thereby treating the FRDA-associated pneumonia in the subject.

FRDA-Associated Hypertrophic Cardiomyopathy

Hypertrophic cardiomyopathy is a condition in which the muscles of the heart thicken, making it difficult for the heart to pump blood through the circulatory system. It can be caused by a deficiency in FXN in the mitochondria of the heart cells. In subjects diagnosed with FRDA, progressive hypertrophic cardiomyopathy about 50% of the time progresses to heart failure and death. Protein replacement therapy with a disclosed TAT-FXN fusion polypeptide can replace the FXN deficiency underlying hypertrophic cardiomyopathy.

Administration of a disclosed pharmaceutical composition comprising a disclosed TAT-FXN fusion polypeptide, can therefore be effective as a protein replacement therapy in FXN-deficient subjects diagnosed with both FRDA and hypertrophic cardiomyopathy. Accordingly, the present disclosure provides methods of treating an FRDA-associated hypertrophic cardiomyopathy in a subject, comprising administering to a subject in need thereof a pharmaceutical composition comprising a TAT-FXN fusion polypeptide of the disclosure, thereby treating the FRDA-associated hypertrophic cardiomyopathy in the subject.

Diabetes

The hallmark of diabetes is an inability to properly regulate blood levels of glucose, resulting in elevated blood glucose levels. In subjects diagnosed with FRDA, diabetes often shows up as a consequence of FXN-deficient mitochondria in the pancreas. Protein replacement therapy with a disclosed TAT-FXN fusion polypeptide can replace the FXN deficiency underlying diabetes.

Administration of a disclosed pharmaceutical composition comprising a disclosed TAT-FXN fusion polypeptide, can therefore be effective as a protein replacement therapy in FXN-deficient subjects diagnosed with diabetes. Accordingly, the present disclosure provides methods of treating an FRDA-associated diabetes in a subject, comprising administering to a subject in need thereof a pharmaceutical composition comprising a TAT-FXN fusion polypeptide of the disclosure, thereby treating the FRDA-associated diabetes in the subject.

Other FRDA-Associated Diseases/Disorders

Subjects diagnosed with FRDA often experience other disorders associated with FXN deficiency. Such FRDA-associated disorders can include, without limitation: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low high-density lipoprotein (HDL) cholesterol, and elevated low-density lipoprotein (LDL) cholesterol; scoliosis that requires surgery to correct; and/or combinations thereof. Protein replacement therapy with a disclosed TAT-FXN fusion polypeptide can replace the FXN deficiency underlying these diseases/disorders.

Administration of a disclosed \pharmaceutical composition comprising a disclosed TAT-FXN fusion polypeptide, can therefore be effective as a protein replacement therapy in FXN-deficient subjects diagnosed with FRDA and experiencing neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; scoliosis that requires surgery to correct; and/or combinations thereof.

Accordingly, the present disclosure provides methods of treating an FRDA-associated disease, disorder or condition, comprising administering to a subject in need thereof a pharmaceutical composition comprising a TAT-FXN fusion polypeptide of the disclosure, wherein the FRDA-associated disease, disorder or condition is selected from: neurological disorders including, without limitation, loss of proprioception, loss of reflexes, loss of ability to walk, loss of ability to hold gaze with eyes; impaired swallowing and/or a progressive loss of the ability to swallow; progressive loss of hearing; progressive loss of vision due to retinal degeneration from lack of FXN; progressive loss of speech; metabolic syndrome including, without limitation, elevated triglycerides, low HDL cholesterol, and elevated LDL cholesterol; and scoliosis that requires surgery to correct.

In some embodiments, the present disclosure also provides methods of treating FRDA, including, e.g., an FRDA-associated disease, disorder or condition, that comprise administering to a subject in need thereof a pharmaceutical composition comprising a pharmaceutically acceptable vehicle, carrier and/or excipient and the disclosed TAT-FXN fusion polypeptide, e.g., TAT-FXN fusion polypeptide comprising, or consisting of, SEQ ID NO: 1, at a concentration of greater than or equal to 10 mg/mL. For example, the method may comprise administering to a subject in need thereof the pharmaceutical composition as described herein, wherein the disclosed TAT-FXN fusion polypeptide is present in the pharmaceutical composition at a concentration of greater than about 10 mg/mL or greater than or equal to: about 15 mg/mL, about 20 mg/mL, about 25 mg/mL, about 30 mg/mL, about 35 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL or about 100 mg/mL. In some embodiments, a disclosed TAT-FXN fusion polypeptide may be present in the pharmaceutical composition at a concentration of about 5 mg/mL to about 25 mg/mL, about 15 mg/mL to about 30 mg/mL, about 20 mg/mL to about 50 mg/mL, about 25 mg/mL to about 60 mg/mL, about 35 mg/mL to about 75 mg/mL, about 50 mg/mL to about 80 mg/mL or about 90 mg/mL to about 100 mg/mL. In some embodiments, a disclosed TAT-FXN fusion polypeptide may be present in the pharmaceutical composition at a concentration of about 40 mg/mL to about 60 mg/mL, about 40 mg/mL to about 55 mg/mL, about 45 mg/mL to about 60 mg/mL, about 45 mg/mL to about 55 mg/mL, about 46 mg/mL to about 54 mg/mL, about 47 mg/mL to about 53 mg/mL, about 48 mg/mL to about 52 mg/mL, or about 49 mg/mL to about 51 mg/mL. Alternatively, the disclosed TAT-FXN fusion polypeptide may be present in the pharmaceutical composition at a concentration of about 5 mg/mL to about 50 mg/mL, about 20 mg/mL to about 75 mg/mL or about 25 mg/mL to about 100 mg/mL. In some embodiments, the methods comprise administering the pharmaceutical composition as described herein, wherein the pharmaceutical composition is an injectable pharmaceutical composition, e.g., suitable for subcutaneous administration.

Administration and Dosing

The pharmaceutical compositions comprising a TAT-FXN fusion polypeptide disclosed herein can be administered to a subject by injection. Injection may be intravenous, subcutaneous, intraperitoneal, intramuscular or intradermal. Injectable preparations, for example sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

In various aspects, a disclosed pharmaceutical composition comprising a TAT-FXN fusion polypeptide is administered by subcutaneous injection. Subcutaneous injections are typically administered as a bolus into the layer of skin directly below the dermis. As there are few blood vessels in this location, a pharmaceutical ingredient administered to this location will typically release slowly, over time, providing a sustained rate of absorption of a disclosed TAT-FXN fusion polypeptide into the subject.

An injection given intravenously is typically in the range of 5-20 mL in volume. In contrast, an injection given subcutaneously is typically only between 0.05 to 1 mL in volume, typically with a maximum volume of about 1.5 mL, and therefore the concentration of the pharmaceutical ingredient in such an injection must be sufficiently high to achieve a desired therapeutic effect. In that regard, the improved solubility demonstrated by a disclosed TAT-FXN fusion polypeptide herein is advantageous as it will allow for greater concentration when in solution, thereby accommodating administration via subcutaneous injection. In addition, the high concentrations achieved by the pharmaceutical compositions provided herein, e.g., at least 10 mg/mL, such as about 50 mg/mL of the TAT-FXN fusion polypeptide, are advantageous as they accommodate administration of desirable, i.e., therapeutic, amounts of TAT-FXN fusion polypeptide via subcutaneous injection.

Administration by injection typically requires a peptide to be formulated in a manner that is pharmaceutically acceptable for injection into a subject, which in some embodiments is a human. In some embodiments, a disclosed TAT-FXN fusion polypeptide is formulated for subcutaneous injection by dissolution in a pharmaceutically acceptable vehicle. In various aspects, the pharmaceutically acceptable vehicle may also include one or more excipients.

There are a number of suitable pharmaceutically acceptable vehicles that may be of use in a pharmaceutical formulation of a disclosed TAT-FXN fusion polypeptide. Suitable vehicles include, for example, water, saline solution, sodium acetate, acetic acid-sodium acetate buffer, phosphate-buffered saline, oil emulsions and the like. The emulsions include oil-in-water emulsions with oil as the dispersed phase and water-in-oil emulsions with oil as the continuous phase. The oil can be of vegetable or origin or synthetically produced. Suitably, the vegetable oil of the emulsions is soybean oil or safflower oil, or any combination thereof. In some embodiments, the vehicle is sodium acetate.

There are a number of suitable pharmaceutically acceptable excipients that may be of use in a pharmaceutical formulation of a disclosed TAT-FXN fusion polypeptide. In some embodiments, the pharmaceutically acceptable excipient is propylene glycol.

Thus, in one aspect the present disclosure provides a pharmaceutical composition for administration to a subject via subcutaneous injection, comprising: (a) a therapeutically effective amount of a disclosed TAT-FXN fusion polypeptide; (b) one or more pharmaceutically acceptable vehicles; and (c) a pharmaceutically acceptable excipient.

The pH of the pharmaceutical composition can vary. In various aspects, it is desirable to maintain the pH of the pharmaceutical composition at physiologic levels, for example at a pH between about 5-7, between about 5-6, between about 5.5-6.5, or between about 6-7. In one embodiment, the pH of the pharmaceutical composition is about 5, about 5.5, about 6, about 6.5 or about 7. In one embodiment, the pH of the pharmaceutical composition is about 5. In one embodiment, the pH of the pharmaceutical composition is between about 5-6. In one embodiment, the pH of the pharmaceutical composition is between about 5.5-6.5. In one embodiment, the pH of the pharmaceutical composition is between about 5.6 and 6. In one embodiment, the pH of the pharmaceutical composition is between about 5.7 and 5.9. In one embodiment, the pH of the pharmaceutical composition is about 5.8. In one embodiment, the pH of the pharmaceutical composition is about 6.0.

Another pharmaceutical composition can comprise a disclosed TAT-FXN fusion polypeptide at a concentration of greater than or equal to 2 mg/mL and a pharmaceutically acceptable vehicle, carrier and/or excipient. For example, a disclosed TAT-FXN fusion polypeptide may be present in the pharmaceutical composition at a concentration of greater than or equal to: about 10 mg/mL, about 15 mg/mL, about 20 mg/mL, about 25 mg/mL, about 30 mg/mL, about 35 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL or about 100 mg/mL. In some embodiments, a disclosed TAT-FXN fusion polypeptide may be present in the pharmaceutical composition at a concentration of about 5 mg/mL to about 25 mg/mL, about 15 mg/mL to about 30 mg/mL, about 20 mg/mL to about 50 mg/mL, about 25 mg/mL to about 60 mg/mL, about 35 mg/mL to about 75 mg/mL, about 50 mg/mL to about 80 mg/mL, or about 90 mg/mL to about 100 mg/mL. Alternatively, a disclosed TAT-FXN fusion polypeptide may be present in the pharmaceutical composition at a concentration of about 5 mg/mL to about 50 mg/mL, about 20 mg/mL to about 75 mg/mL, or about 25 mg/mL to about 100 mg/mL. A pharmaceutical composition can be an injectable pharmaceutical composition, which in further embodiments is suitable for subcutaneous administration.

A pharmaceutically acceptable vehicle may be an aqueous vehicle, such as, for example, water, a saline solution or an aqueous buffer, such as an acetate buffer or a phosphate buffer. In a preferred embodiment, the buffer is a histidine buffer. A disclosed TAT-FXN fusion polypeptide present in the pharmaceutical composition is fully dissolved in the pharmaceutically acceptable vehicle. The term "fully dissolved in the pharmaceutical composition", as used herein, refers to a pharmaceutical composition that comprises a disclosed TAT-FXN fusion polypeptide and that is a clear solution and/or does not comprise a visible precipitate.

Preparation of a pharmaceutical composition comprising a disclosed TAT-FXN fusion polypeptide which comprises a concentration of greater than 10 mg/mL, e.g., 50 mg/mlL, is based on the surprising discovery that it is possible to prepare compositions (e.g., aqueous compositions) comprising a disclosed TAT-FXN fusion polypeptide at concentrations of at or greater than about 50 mg/mL by using the buffer, surfactant, pharmaceutically acceptable excipient and at the optimal pH, as disclosed herein. The pharmaceutical compositions provided herein comprise a disclosed TAT-FXN fusion polypeptide at a concentration of greater than about 10 mg/mL, e.g., about 50 mg/mL, allow for administration of a disclosed TAT-FXN fusion polypeptide to a subject by subcutaneous injection in an amount of greater than or equal to 10 mg/injection. For example, a disclosed TAT-FXN fusion polypeptide may be administered by subcutaneous injection to a subject in an amount greater than or equal to: 10 mg/injection, 15 mg/injection, 20 mg/injection, 25 mg/injection, 30 mg/injection, 35 mg/injection, 40 mg/injection, 45 mg/injection, 50 mg/injection, 55 mg/injection, 60 mg/injection, 65 mg/injection, 70 mg/injection, 75 mg/injection, 80 mg/injection, 85 mg/injection, 90 mg/injection, 95 mg/injection or 100 mg/injection. For example, a disclosed TAT-FXN fusion polypeptide may be administered by subcutaneous injection to a subject in an amount greater than or equal to: 50 mg/injection. For example, a disclosed TAT-FXN fusion polypeptide may be administered by subcutaneous injection to a subject in an amount of about 2 mg/injection to about 150 mg/injection, about 2 mg/injection to about 100 mg/injection, about 10 mg/injection to about 150 mg/injection, about 20 mg/injection to about 150 mg/injection, about 5 mg/injection to about 25 mg/injection, about 15 mg/injection to about 30 mg/injection, about 20 mg/injection to about 50 mg/injection, about 25 mg/injection to about 60 mg/injection, about 35 mg/injection to about 75 mg/injection, about 50 mg/injection to about 80 mg/injection, about 90 mg/injection to about 120 mg/injection, and/or about 100 mg/injection to about 150 mg/injection. A disclosed TAT-FXN fusion polypeptide may be present in the pharmaceutical composition at a concentration of about 5 mg/injection to about 50 mg/injection, about 20 mg/injection to about 75 mg/injection, about 25 mg/injection to about 100 mg/injection or about 50 mg/injection to about 150 mg/injection.

Dosing of a disclosed TAT-FXN fusion polypeptide may vary from subject to subject, based on an individual subject's sensitivity to a disclosed TAT-FXN fusion polypeptide, tolerance to the amount dosed over time, and the like. Generally, the amount of a disclosed TAT-FXN fusion polypeptide administered to a subject can range from about 5 mg kg$^{-1}$ to about 60 mg kg$^{-1}$ per day, based on the milligrams of the active composition in a given formulation per kilogram of the subject's body weight. The total dose may be administered at once, as a single dose, or may be split among two or more doses, administered multiple times per day, as necessary to affect a desired therapeutic effect. In some cases, three or more doses of a disclosed TAT-FXN fusion polypeptide may be administered to a given patient in any one 24 hour period; fewer doses may be administered to patients who respond well to the therapy.

Generally, a subject will be administered a starting dose that is regarded as safe by a health care provider, and the dose will be titrated up or down, based on the individual subject's tolerance and tissue levels of FXN to achieve a desired therapeutic effect. For example, a recommended starting dose for a subject may be 30 mg kg$^{-1}$, administered subcutaneously 3 times per day. The health care provider will administer this dose and then monitor levels of a disclosed TAT-FXN fusion polypeptide by taking skin biopsies and measuring the amount of a disclosed TAT-FXN fusion polypeptide present therein. The amount present will be compared to a known baseline, for example that as seen in a healthy subject, and the dose of a disclosed TAT-FXN fusion polypeptide will be titrated incrementally or decrementally as needed to maintain skin levels at a target amount and/or to achieve a desired therapeutic benefit, up to a maximum dose of 60 mg kg$^{-1}$ daily. A dose can be titrated at 1-day, 1-week, or longer intervals.

In some embodiments, a TAT-FXN fusion polypeptide of the present disclosure may be administered to a subject at a dose of about 10-mg to about 150 mg, e.g., about 10 mg to about 30 mg, about 20 mg to about 75 mg, about 50 mg to about 100 mg, or about 100 mg to about 150 mg. For example, the TAT-FXN fusion polypeptide may be administered to a subject at a dose of about 25 mg, about 50 mg, about 75 mg, about 100 mg or about 150 mg. In some embodiments, the dose may be administered once per day. In some embodiments, a TAT-FXN fusion polypeptide of the present disclosure may be administered to a subject at a dose of about 5 mg kg$^{-1}$ to about 60 mg kg$^{-1}$ per day, e.g., about 10 mg kg$^{-1}$ to 50 mg kg$^{-1}$ per day, about 20 mg kg$^{-1}$ to 40 mg kg$^{-1}$ per day, about 30 mg kg$^{-1}$ to 40 mg kg$^{-1}$ per day, about 40 mg kg$^{-1}$ to 50 mg kg$^{-1}$ per day, about 50 mg kg$^{-1}$ to 60 mg kg$^{-1}$ per day, about 5 mg kg$^{-1}$ to 10 mg kg$^{-1}$ per day, about 10 mg kg$^{-1}$ to 15 mg kg$^{-1}$ per day, about 15 mg kg$^{-1}$ to 20 mg kg$^{-1}$ per day, about 20 mg kg$^{-1}$ to 25 mg kg$^{-1}$ per day, about 25 mg kg$^{-1}$ to 30 mg kg$^{-1}$ per day, about 30 mg kg$^{-1}$ to 35 mg kg$^{-1}$ per day, about 35 mg kg$^{-1}$ to 40 mg kg$^{-1}$ per day, about 40 mg kg$^{-1}$ to 45 mg kg$^{-1}$ per day, about 45 mg kg$^{-1}$ to 50 mg kg$^{-1}$ per day, about 50 mg kg$^{-1}$ to 55 mg kg$^{-1}$ per day, and about 55 mg kg$^{-1}$ to 60 mg kg$^{-1}$ per day. In some embodiments, a TAT-FXN fusion polypeptide of the present disclosure may be administered to a subject at a dose of about 0.05 mg kg$^{-1}$ to about 20 mg kg$^{-1}$ per day, e.g., about 0.05 mg kg$^{-1}$ to 0.5 mg kg$^{-1}$ per day, about 0.1 mg kg$^{-1}$ to 1 mg kg$^{-1}$ per day, about 0.5 mg kg$^{-1}$ to 5 mg kg$^{-1}$ per day, about 1 mg kg$^{-1}$ to 10 mg kg$^{-1}$ per day, about 2 mg kg$^{-1}$ to 15 mg kg$^{1}$ per day, about 5 mg kg$^{-1}$ to 15 mg kg$^{-1}$ per day or about 10 mg kg$^{-1}$ to about 10 mg kg$^{-1}$ per day.

In addition to the skin biopsies referenced above, criteria for determining the effective dose for a given subject include monitoring the symptoms displayed and/or reported by the subject during treatment. Prior to commencing treatment with a disclosed TAT-FXN fusion polypeptide, subjects will undergo, or will have already undergone, an extensive medical evaluation. A typical medical evaluation for subjects diagnosed with Friedreich's Ataxia may include measuring one or more of the following: neurologic function, cardiac function, gross and fine motor skills, hearing, speech, vision, blood work for diabetes, and swallowing.

The results of evaluations performed before treatment may serve as baseline for evaluating the effectiveness of the administered treatment. This 'baseline' evaluation may be part of the process of designing and adjusting a proper dosing regimen for any given subject. The administered dose can be increased or decreased as necessary to affect a desirable therapeutic effect in a subject. Elements of the dosing evaluation may include feedback from the subject regarding changes in mobility, balance, sensation, mood, fatigue, stamina, strength, and any other physiological or psychological trait associated with a diagnosis of Friedreich's Ataxia.

The pharmaceutical compositions provided by the present disclosure may be formulated in consideration of any one or more of the following: ease of storage, transportation, stability and patient convenience. Formulations may include preloaded syringes, vial, bottle, and the like. In some embodiments, a disclosed TAT-FXN fusion polypeptide may be lyophilized and placed into a sterile vial for storage and/or transportation. To generate a pharmaceutical composition, the lyophilized peptide may be admixed with a sterile vehicle and/or sterile excipient to create a pharmaceutical composition suitable for subcutaneous administration.

A TAT-FXN fusion polypeptide or a pharmaceutical composition disclosed herein can be used in the manufacture (i.e., preparation) of a medicament for administration to a subject. The medicament is a therapeutic composition including a TAT-FXN fusion polypeptide or a pharmaceutical composition provided herein. The pharmaceutical composition can be the same as the medicament.

EXAMPLES

Example 1. Development of a Pharmaceutical Composition Comprising a TAT-FXN Fusion Polypeptide Summary Pre-formulation development studies for a TAT-FXN fusion polypeptide of SEQ ID NO: 1 were performed to evaluate suitable formulation conditions that facilitate conformational, physical, chemical and thermal stability of the TAT-FXN fusion polypeptide. A key objective was to develop a pharmaceutical composition in which the TAT-FXN fusion polypeptide of SEQ ID NO: 1 would be present at a high concentration of about 50 mg/mL or greater, e.g., about 50 mg/mL to about 100 mg/mL, or greater.

Conformational and thermal stability of the TAT-FXN fusion polypeptide was initially evaluated using a panel of candidate buffers over the pH range 4.5 to 8.0, including acetate, succinate, citrate, histidine, phosphate and Tris. A subset of the tested formulations comprising acetate, histidine, and tris with pH ranging from 5.0 to 7.5 were selected based on their performance.

These buffers in conjunction with a panel of excipients, including sucrose, mannitol, sodium chloride (NaCl), arginine and proline, were evaluated for their ability to enhance stability of the TAT-FXN fusion polypeptide. From the excipient screen, two buffer types (histidine and Tris) and five excipient combinations (1) sucrose, (2) mannitol, (3) mannitol and calcium chloride, (4) calcium chloride, and (5) proline were selected for further evaluation. In the subsequent solubility study, the aforementioned buffer and excipient combinations all achieved ≥130 mg/mL concentration of the TAT-FXN fusion polypeptide, with largely comparable SLS and SEC results. It is worthwhile to note these high concentration samples all showed brown coloration. Given the workability of a 100 mg/mL concentration level and the goal for developing a high concentration liquid formulation, the subsequent studies were performed at 100 mg/mL of the TAT-FXN fusion polypeptide. From the solubility screen, two buffer types (histidine and Tris) and three excipient combinations (sucrose, mannitol, and mannitol with calcium chloride) were selected for further evaluation. Surfactant screen showed that polysorbate 20 (PS20) at 0.05% is generally beneficial with no clear indication of having a negative effect on the TAT-FXN fusion polypeptide, and thus was included in the final formulation evaluation. Lastly, a final Design of Experiment (DOE) study was conducted to differentiate and select the best buffer type, excipient class/types, and pH. After statistical analysis of the resulting data, two top candidate formulations were identified as follows: (1) 20 mM histidine, 250 mM sucrose, 0.05% PS20, pH 5.8; and (2) 20 mM histidine, 250 mM mannitol, 0.05% PS20, pH 5.8.

Methods

Appearance

Liquid sample appearance was evaluated against a clean white and black background in diffuse laboratory lighting. Each sample was tested for color and clarity (opalescence).

Protein Content

Protein content was measured using UV-Visible Spectroscopy. The concentration was measured for samples using extinction coefficient of 1.742 mL mg-1 cm-1 at 280 nm wavelength.

Turbidity

Turbidity was measured using UV-Visible Spectroscopy. Samples were analyzed without dilution at 340 nm. Samples were also analyze using isothermal light scattering at 266 nm and at 473 nm using the Uncle instrument.

pH Measurements pH measurements of all sample solutions were performed using a calibrated SevenMulti Meter (Mettler Toledo) with an automatic temperature compensation electrode.

Differential Scanning Fluorimetry and Static Light Scattering

The thermal stability of the TAT-FXN fusion polypeptide formulations was monitored by differential scanning fluorimetry (DSF). Melting temperature ($T_m$) data was collected using an Unchained Laboratories UNit instrument. The protein samples were analyzed at ~2 mg/mL (diluted in the appropriate buffer-exchange solution, if necessary) and added to UNi mini-quartz cuvettes. Samples were equilibrated at 20° C. for 30 seconds, and the barycentric mean (BCM) of the intrinsic fluorescence spectra from 250-500 nm (266 nm excitation wavelength) was monitored while temperature ramped from 20° C. to 95° C. at a rate of 1° C./minute. The inflection point of the BCM versus temperature curve during an unfolding event (identified by the maximum or minimum of the derivative trace) was identified as the Tm of that transition. Static light scattering (SLS) intensity at 266 nm and 473 nm was also measured in parallel with DSF measurements to observe the onset temperature of small and large aggregate formation ($T_{agg}$), respectively. $T_{agg}$ values were determined by the analysis software as the temperature at which the SLS trace rose to approximately 10% of the scattering signal at the steepest point of the plot.

Dynamic Light Scattering

Dynamic light scattering (DLS) measures time-dependent fluctuations in the intensity of scattered light from particles in a sample, where the Stokes Einstein equation is used to calculate the hydrodynamic radius of the particle(s) in solution. The DLS experiments for TAT-FXN fusion polypeptide formulation samples were performed using 40 μL of neat sample (if concentration is 2 mg/mL) or sample diluted to 2 mg/mL in formulation buffer without surfactant using a DynaPro Plate Reader II instrument (Wyatt). Bracketing BSA preparations (2 mg/mL) were used to confirm system suitability. Each sample was analyzed both uncentrifuged and after centrifugation at ~16000 rcf for 5 minutes. A total of 10 individual scans were performed at 25° C., with an acquisition time of 5 seconds for each sample. The percent acquisitions unmarked (or the number of scans able to be suitably fit by cumulants analysis) was reported. Low percent acquisitions unmarked is suggestive of the presence of large particulate matter, which complicates the fitting of the correlation curve. Viscosity was set to that of phosphate buffered saline, 1.019 cP. The resultant intensity distribution plots were compared to evaluate the effects of various formulation components on mean particle size by intensity (overall diameter), a global size distribution width parameter (overall percent polydispersity, or % Pd), the average peak diameter of the TAT-FXN fusion polypeptide monomer (Peak 2 diameter), and that peak's width parameter (Peak 2% Pd). Percent polydispersity (overall or Peak 2) is a width parameter that reflects the heterogeneity detected in the intensity distribution plot, where % Pd<20% is indicative of a near-monodisperse solution and/or species conformation.

Viscosity

Rheometer-based viscosity measurements were performed using the Brookfield DV-III Ultra Programmable Rheometer. Briefly, a DV-III Ultra Programmable Rheometer was calibrated with Brookfield Viscosity Standard Fluid #10 and 0.5 mL of each sample was measured at various spindle speeds (shear rates). Samples displaying viscosity (cP) readings with <10% RSD for all shear rates were considered Newtonian over this range, while samples with shear rate-dependent viscosity values were considered non-Newtonian.

Osmolality

Osmolality measurements were performed using a multi-osmette 2430 automatic osmometer, which measures osmolality in liquid solutions by measuring freezing point depression. Analysis was performed using a Precision systems multi-osmette Osmometer (model 2430).

Other Analyses

Size Exclusion Chromatography (SEC), Reversed-Phase High Performance Liquid Chromatography (RP-HPLC), Cation Exchange Chromatography (CEX), Non-Reduced and Reduced Capillary Gel Electrophoresis (CGE) were performed according to previously developed procedures for analyzing the TAT-FXN fusion polypeptide of SEQ ID NO: 1.

Results and Discussion

Baseline Buffer Evaluation

The thermal and conformational stability of the TAT-FXN fusion polypeptide of SEQ ID NO: 1 was evaluated over a pH range of 4.0 to 8.0 in the presence of candidate buffers listed in Table 1 below.

TABLE 1

Candidate Buffers and Formulations

| Formulation | Buffer | pH |
| --- | --- | --- |
| A | 20 mM succinate | 4.0 |
| B | | 5.0 |
| C | | 6.0 |
| D | 20 mM acetate | 4.0 |
| E | | 5.0 |
| F | 20 mM citrate | 5.0 |
| G | | 6.0 |
| H | | 7.0 |
| I | 20 mM histidine | 6.0 |
| J | | 7.0 |
| K | 20 mM phosphate | 6.5 |
| L | | 7.5 |
| M | 20 mM Tris | 7.5 |
| N | | 8.5 |

This study was conducted using the TAT-FXN fusion polypeptide batch formulated at 8.5 mg/mL in 50 mM acetate and 1% polypropylene glycol at pH 5.0. Protein samples were buffer exchanged using Amicon Ultra Centrifugal Filters (10 kDa NMWL Ultracel regenerated cellulose membrane, Millipore C/N UFC901096). In each pre-rinsed concentrator, 221 μL of the TAT-FXN fusion polypeptide were combined with ~15 mL of the appropriate buffer. Samples were centrifuged at 4000×g until a volume of ~500 μL was achieved. A volume of 5 mL of the appropriate buffer was then added to each centrifugal filter. Samples were again centrifuged at 4000×g until a volume of ~500 μL was achieved for a >800-fold exchange. A total of 26 mg of material was consumed for the study.

The protein concentration in the samples was measured by Solo-VPE using an extinction coefficient of 1.742 ml/mg*cm. Due to sample volume limitation, samples were diluted 10-fold in 0.9% NaCl. Results are shown in Table 2 below.

TABLE 2

Baseline Buffer Screen: Post Buffer Exchange Protein Concentration

| Formulation | Buffer | pH | Protein Concentration (µg/mL) | Recovered Volume (µL) | % Recovery |
|---|---|---|---|---|---|
| A | 20 mM succinate | 4.0 | 3.5 | 470 | 87 |
| B | | 5.0 | 3.0 | 480 | 75 |
| C | | 6.0 | 2.0 | 470 | 50 |
| D | 20 mM acetate | 4.0 | 2.9 | 480 | 75 |
| E | | 5.0 | 2.9 | 480 | 75 |
| F* | 20 mM citrate | 5.0 | 0.6 | 460 | 14 |
| G* | | 6.0 | 0.3 | 400 | 5 |
| H* | | 7.0 | 0.2 | 470 | 4 |
| I | 20 mM histidine | 6.0 | 3.1 | 480 | 78 |
| J | | 7.0 | 3.5 | 470 | 88 |
| K* | 20 mM phosphate | 6.5 | 1.1 | 500 | 30 |
| L* | | 7.5 | 0.5 | 520 | 15 |
| M | 20 mM Tris | 7.5 | 3.2 | 470 | 80 |
| N | | 8.5 | 2.4 | 500 | 64 |

*observed precipitation (cloudy samples after buffer exchange)

The results presented in Table 2 indicate that all formulations comprising citrate and phosphate demonstrated low recoveries, ≤30% as compared to other formulations which exhibited ≥50% recoveries. Additionally, the original source material was diluted 4.25-fold in PPG-free 50 mM Acetate pH 5.0 buffer to generate a sample designated as sample "O" within this study. Though sample O was expected to exhibit similar characteristics as sample E, the former was not subjected to the potential stress of buffer exchange and still contained traces of PPG.

Samples were normalized to 2 mg/mL by dilution with the appropriate buffer prior to analysis. Low concentration samples were not manipulated further. Thermal and conformational stability of the protein in various buffers was determined at 2 mg/mL using Differential Scanning Fluorimetry (DSF), Dynamic Light Scattering (DLS), and Static Light Scattering (SLS). DSF was used to assess the thermal stability of the TAT-FXN fusion polypeptide by measuring changes in the intrinsic amino acid fluorescence. SLS was collected by measuring the scatter intensity at 90° angle and the intensity increases with aggregation. Conversely, marked and sharp drop in intensity indicate the formation of insoluble aggregates. DLS analysis yielded information about the distribution and size of particles in each formulation. Formulations exhibiting the best combined attributes for thermal and conformational stability were selected for further evaluation.

Differential Scanning Fluorimetry and Static Light Scattering

Differential Scanning Fluorimetry (DSF) was used to determine the temperature at which an unfolding event (Tm) was observed. Furthermore, the aggregation ($T_{agg}$) patterns determined by SLS at 266 nm (smaller aggregates) and 473 nm (larger aggregates) were evaluated for the TAT-FXN fusion polypeptide in each formulation. $T_m$ results for the TAT-FXN fusion polypeptide sample formulations (average of three replicates) are presented in Table 3 below.

TABLE 3

Baseline Buffer Screen: DSF Results

| Formulation | Buffer | pH | Average $T_m$ (° C.) | % RSD |
|---|---|---|---|---|
| A | 20 mM succinate | 4.0 | 39.1 | 1 |
| B | | 5.0 | 53.8 | 1 |
| C* | | 6.0 | 53.3 | 1 |
| D | 20 mM acetate | 4.0 | 47.3 | 2 |
| E | | 5.0 | 63.4 | 1 |
| F* | 20 mM citrate | 5.0 | 49.2 | 1 |
| G* | | 6.0 | 57.3 | 2 |
| H* | | 7.0 | 57.7 | 2 |
| I | 20 mM histidine | 6.0 | 66.2 | 1 |
| J | | 7.0 | 67.4 | 2 |
| K* | 20 mM phosphate | 6.5 | 57.0 | 2 |
| L* | | 7.5 | 54.3 | 2 |
| M | 20 mM Tris | 7.5 | 63.0 | 1 |
| N | | 8.5 | 61.7 | 2 |
| O | 50 mM acetate (PPG trace) | 5.0 | 59.4 | 4 |

*≤50% recovery post buffer exchange

The results presented in Table 3 indicate that melting temperatures of 60° C. or greater were observed for histidine buffer at pH 6.0 and 7.0; Tris buffer at pH 7.5 and 8.5; and acetate buffer at pH 6.0. A general trend of increasing $T_m$ with increasing pH was observed in the pH range of 4 to 6, but 7 or 8 did not confer any improved thermal stability compared to pH 6. It is noted that Tris buffers, known to exhibit pronounced pH decreases with increasing temperature were prepared at room temperature, and were therefore at lower pH than reported at those melting temperatures.

The $T_{agg}$ results for 266 nm are presented in Table 4 below (average of three replicates).

TABLE 4

Baseline Buffer Screen: $T_{agg}$ 266 nm Results

| Formulation | Buffer | pH | Average $T_{agg}$ from 266 nm SLS (° C.) | % RSD (pre-mask) |
|---|---|---|---|---|
| A | 20 mM succinate | 4.0 | 26.9 | 1 |
| B | | 5.0 | 42.9 | 2 |
| C* | | 6.0 | 25.1 | 2 |
| D | 20 mM acetate | 4.0 | 27.0 | 3 |
| E | | 5.0 | 26.7 | 1 |
| F* | 20 mM citrate | 5.0 | 27.0 | 2 |
| G* | | 6.0 | 32.3 | 24 |
| H* | | 7.0 | 27.3 | 12 |
| I | 20 mM histidine | 6.0 | 26.4 | 2 |
| J | | 7.0 | 26.7 | 2 |
| K* | 20 mM phosphate | 6.5 | 24.9 | 4 |
| L* | | 7.5 | 24.9 | 2 |
| M | 20 mM Tris | 7.5 | 48.5 | 5 |
| N | | 8.5 | 27.3 | 4 |
| O | 50 mM acetate (PPG trace) | 5.0 | 23.1 | 2 |

*≤50% recovery post buffer exchange

The results presented in Table 4 indicate that Formulations C and K (and, to a lesser degree, F and L) show early significant increases in scattering indicating aggregation, followed by a drop of intensity during further heating (above 55° C.). This is due to the fact that very large protein aggregates precipitate and drop out of solution. SLS is only sensitive to species in solution, therefore upon precipitation the measured intensity drops.

Figure 2:
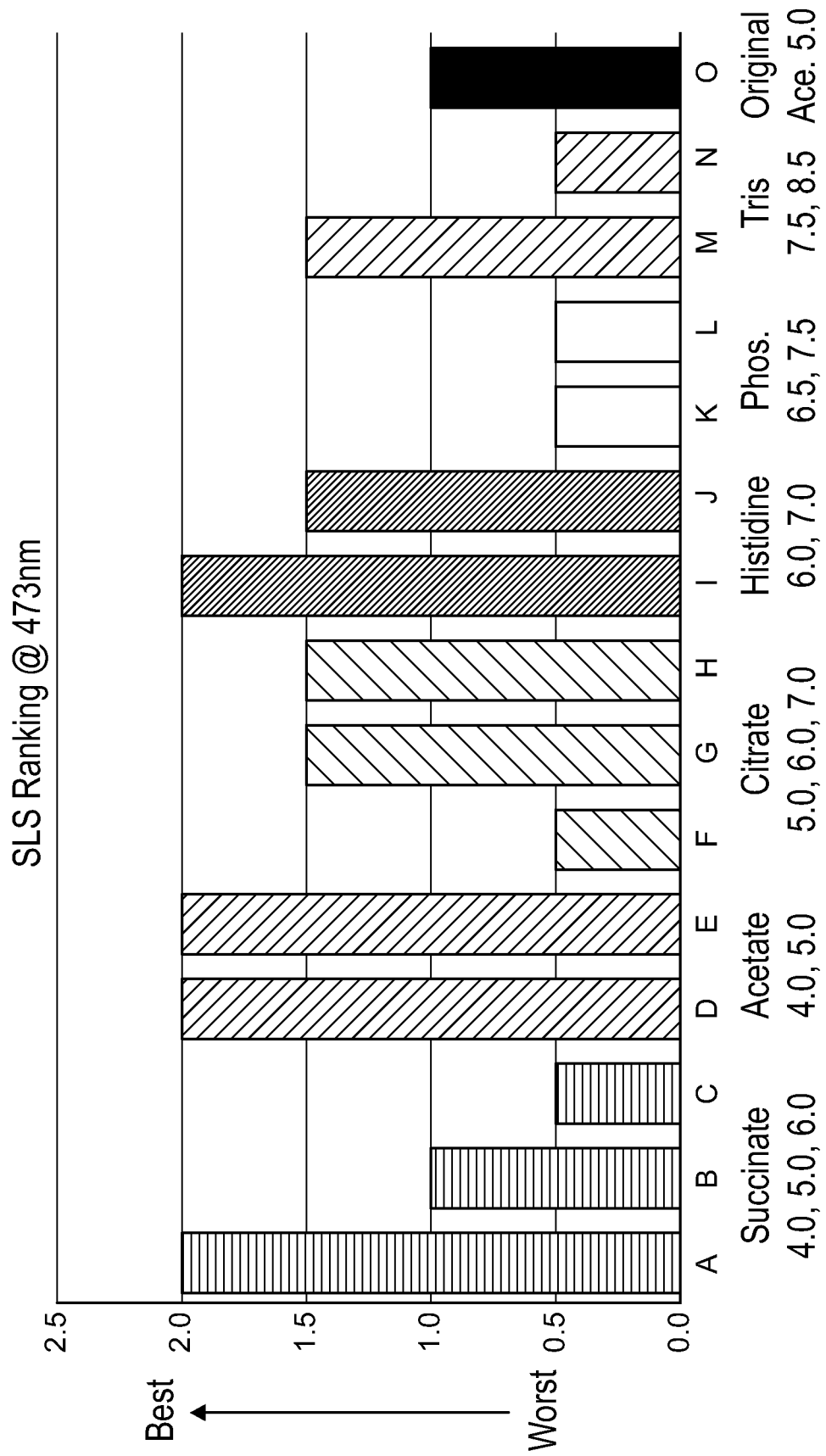
FIG. 2 is a bar graph showing larger aggregate SLS ranking results.

A closer evaluation of the SLS counts vs. Temperature plots show high levels of native light scattering (>110,000 counts at 20° C.) for Formulation N (Tris pH 8.5), despite a reported high $T_{agg}$. In contrast, Formulation I (histidine pH 6.0) light scattering remained below 20,000 counts at 95° C. A different interpretation of the data was warranted to rank the formulations in terms of real aggregation events causing significantly high increases in light scattering (FIG. 1). Based on the re-evaluated ranking, acetate, histidine and succinate formulations were clear top candidates, outperforming the original sample. Similarly, $T_{agg}$ 473 nm result also showed similar trend with regards to observed counts. Formulation rankings based on the $T_{agg}$ 473 data are presented in FIG. 2. The results of the analyses indicate that succinate pH 4.0, acetate pH 4.0 and 5.0, and histidine pH 6.0 formulations were top performers.

Results for citrate and phosphate buffer were superficial due to their significantly lower concentrations and removal of precipitates by centrifugation prior to analysis, thus not included in data analysis. Overall, not only higher pH, but specifically, acetate and histidine formulations confer greater thermal stability to the TAT-FXN fusion polypeptide. Although Tris buffer pH 8.5 performed worse, the aggregation observed in Tris pH 7.5 at ~50° C. is significant enough to point out compared to acetate and histidine formulations. Overall, the best performing formulations were: acetate pH 5.0, histidine pH 6.0 and Tris pH 7.5. The worst performing formulations were: Tris pH 8.5 and succinate.

Dynamic Light Scattering

Light scattering data was collected for baseline buffer screen samples over three replicates. Sample formulations were evaluated for size and particle distribution (overall diameter, peak 2 diameter and polydispersity). The tabulated results are given in Table 5.

The $T_{agg}$ results for 473 nm are presented in Table 5 below (average of three replicates).

TABLE 5

Baseline Buffer Screen: $T_{agg}$ 473 nm Results

| Formulation | Buffer | pH | Average $T_{agg}$ from 473 nm SLS (° C.) | % RSD (pre-mask) |
|---|---|---|---|---|
| A | 20 mM | 4.0 | 26.6 | 2 |
| B | succinate | 5.0 | 50.8 | 1 |
| C* |  | 6.0 | 25.1 | 5 |
| D | 20 mM acetate | 4.0 | 25.5 | 8 |
| E |  | 5.0 | 25.9 | 7 |
| F* | 20 mM citrate | 5.0 | 27.7 | 1 |
| G* |  | 6.0 | 44.8 | 17 |
| H* |  | 7.0 | 30.2 | 1 |
| I | 20 mM | 6.0 | 25.2 | 5 |
| J | histidine | 7.0 | 26.3 | 1 |
| K* | 20 mM | 6.5 | 48.0 | 2 |
| L* | phosphate | 7.5 | 24.9 | 2 |
| M | 20 mM Tris | 7.5 | 27.9 | 3 |
| N |  | 8.5 | 47.8 | 4 |
| O | 50 mM acetate (PPG trace) | 5.0 | 23.4 | 3 |

*≤50% recovery post buffer exchange

Considering protein recoveries ≤50% for formulations C, F, G, H, K and L, those sample's data was not included in data driven conclusions. Monomer peak diameter results are more weighted since overall diameter values are skewed by scattering of larger particles, and therefore do not always accurately reflect the particle size distribution.

Results for citrate and phosphate are superficial due to their significantly lower concentrations and removal of precipitates by centrifugation prior to analysis, thus not included in data analysis. In addition, although succinate pH 6.0 demonstrated relatively lower polydispersity results (both overall and monomer) than other formulations, the 50% protein recovery result from buffer exchange suggests suboptimal conditions for the TAT-FXN fusion protein. Compared to the original sample, acetate formulations exhibited smaller overall diameters. However, most evaluated formulations, except for Tris pH 7.5, were more heterogeneous in particle size than the original sample. Monomer diameter results were encouraging, with acetate pH 5.0, histidine pH 6.0 and 7.0, and Tris pH 7.5 all comparable or more favorable than the original formulation. Furthermore, although all acetate, histidine and Tris pH 7.5 monomer diameter polydispersity values are greater than the original formulation, the results indicate monodisperse species.

In addition to the monomer peak, a ~30 nm aggregate peak was detected in the source material and in most samples of interest (not detected in Succinate pH 5 and Tris pH 8.5), confirming general comparability. Finally, even larger diameter particles were not detected in Succinate pH 4.0, Acetate pH 5.0, Histidine pH 6.0 and Tris pH 7.5. Therefore the best performing formulations were: acetate pH 5.0, histidine pH 7.0, and Tris pH 7.5; the while the worst performing formulation was Tris pH 8.5.

DISCUSSION

Poor protein recoveries from buffer exchange of citrate and phosphate formulations indicate their low compatibility with the TAT-FXN fusion polypeptide. Static light scattering data confirmed this for phosphate formulations. Melting temperatures appeared to be pH dependent to an extent, with no additional stability conferred to the molecule at pH 7 or 8 compared to pH 6. Light scattering data, however, identified high levels of native light scattering (both small particles and larger aggregates) in Tris pH 8.5. Tris pH 7.5 showed a clear aggregation event at ~50° C. but outperformed the original formulation. Succinate UNit results exhibited a clear increase in thermal stability as well as propensity to aggregate with increasing pH. Succinate pH 4.0 performed well by Dynamic light scattering. DLS data supported acetate pH 5.0, Histidine pH 6.0 and Histidine pH 7.0 as favorable buffers and suggested Tris pH 7.5 as a comparable candidate with regards to polydispersity and monomer diameter. Overall, 20 mM acetate pH 5.0 and histidine (both pH 6.0 and 7.0) outperformed the original formulation (50 mM Acetate pH 5.0 with trace amounts of PPG), and were selected for further evaluation in the subsequent excipient study. Tris pH 7.5 could also be evaluated further in combination with excipients.

Excipient Screening

The stability of the TAT-FXN fusion polypeptide was evaluated in the presence of various excipients, including sodium chloride, sucrose, mannitol, arginine and proline, using the buffering formulations selected as a result of baseline buffer screening (20 mM acetate pH 5.0, 20 mM histidine, pH 6.0, 20 mM Tris pH 7.5). The formulations used for the excipient evaluation are presented in Table 6 below.

TABLE 6

Excipient Screen: Formulations

| Formulation | Buffer | Excipient |
|---|---|---|
| A | 20 mM acetate | 150 mM NaCl |
| B | pH 5.0 | 250 mM sucrose |
| C |  | 250 mM mannitol |
| D |  | 150 mM arginine |
| E |  | 250 mM proline |

TABLE 6-continued

Excipient Screen: Formulations

| Formulation | Buffer | Excipient |
|---|---|---|
| F | 20 mM histidine pH 6.0 | 150 mM NaCl |
| G | | 250 mM sucrose |
| H | | 250 mM mannitol |
| I | | 150 mM arginine |
| J | | 250 mM proline |
| K | 20 mM Tris pH 7.5 | 150 mM NaCl |
| L | | 250 mM sucrose |
| M | | 250 mM mannitol |
| N | | 150 mM arginine |
| O | | 250 mM proline |
| P | | 50 mM acetate pH 5.0, 1% PPG |

In addition, the original sample was also buffer exchanged in 50 mM Acetate pH 5.0, 1% PPG. The target protein concentration for the study was 2 mg/mL. Protein samples were buffer exchanged using Amicon Ultra Centrifugal Filters (10 kDa NMWL Ultracel regenerated cellulose membrane, Millipore C/N UFC901096). To each pre-rinsed concentrator, 294 µL of 8.5 mg/mL TAT-FXN fusion polypeptide were combined with 14.5 mL of the appropriate buffer. Samples were centrifuged at 4000×g until a volume of ~700 µL was achieved. A volume of 12 mL of the appropriate buffer was then added to each centrifugal filter. Samples were again centrifuged at 4000×g until a volume of ~700 µL was achieved for a >800-fold exchange. The concentration of the TAT-FXN fusion polypeptide in the samples was measured in duplicate by solo-VPE, using an extinction coefficient of 1.742 ml/mg*cm, prior to normalizing to 2 mg/mL using the appropriate buffer. Recovery results are shown in Table 7 below.

TABLE 7

Excipient Screen: Post Buffer Exchange Protein Concentration

| Formulation | Buffer | Excipient | Protein Concentration (µg/mL) | Recovered Volume (µL) | % Recovery |
|---|---|---|---|---|---|
| A* | 20 mM acetate pH 5.0 | 150 mM NaCl | 1.4 | 700 | 39 |
| B | | 250 mM sucrose | 2.5 | 750 | 75 |
| C | | 250 mM mannitol | 2.8 | 720 | 81 |
| D* | | 150 mM arginine | 1.5 | 750 | 46 |
| E | | 250 mM proline | 2.1 | 760 | 65 |
| F* | 20 mM histidine pH 6.0 | 150 mM NaCl | 1.1 | 700 | 31 |
| G | | 250 mM sucrose | 2.8 | 800 | 89 |
| H | | 250 mM mannitol | 2.4 | 700 | 68 |
| I* | | 150 mM arginine | 1.5 | 800 | 48 |
| J | | 250 mM proline | 2.5 | 750 | 74 |
| K* | 20 mM Tris pH 7.5 | 150 mM NaCl | 0.5 | 750 | 14 |
| L | | 250 mM sucrose | 2.2 | 750 | 67 |
| M | | 250 mM mannitol | 2.2 | 800 | 70 |
| N* | | 150 mM arginine | 1.3 | 740 | 37 |
| O | | 250 mM proline | 1.9 | 750 | 57 |
| P | | 50 mM acetate pH 5.0, 1% PPG | 2.8 | 700 | 78 |

*observed precipitation (cloudy samples after buffer exchange)

Notably, all NaCl and arginine formulations showed <50% recovery, and due to low sample concentrations, were not further adjusted to 2 mg/mL. Sodium chloride and arginine formulations resulted in protein recovery <50% in all buffer compositions. Furthermore, precipitation was observed in those samples.

Differential Scanning Fluorimetry and Static Light Scattering

Triplicate samples were analyzed with a linear thermal ramp (0.5° C. min$^{-1}$) between 20 and 95° C. with the protein intrinsic fluorescence and static light scattering signals being recorded in triplicate every 1° C., with a hold time of 30 seconds at each temperature to allow equilibration of the samples before measurement started. An exposure time of 1000 ms was used and the two lasers in the system were attenuated to their maximum value. Data analysis was performed using the UNit analysis software, where light scattering signals and fluorescence ratio (barycentric mean-350:330) were plotted against temperature to automatically generate $T_m$ and $T_{agg}$ values. Tabulated results are shown in Table 8 (average of three replicates).

TABLE 8

Excipient Screen: DSF Results

| Formulation | Buffer | Excipient | Average $T_m$ (° C.) | % RSD (pre-mask) |
|---|---|---|---|---|
| A* | 20 mM acetate pH 5.0 | 150 mM NaCl | 44.1 | 10 |
| B | | 250 mM sucrose | 64.4 | 9 |
| C | | 250 mM mannitol | 64.3 | 2 |
| D* | | 150 mM arginine | 51.2 | 1 |
| E | | 250 mM proline | 63.2 | 1 |
| F* | 20 mM histidine pH 6.0 | 150 mM NaCl | 51.3 | 1 |
| G | | 250 mM sucrose | 66.2 | 1 |
| H | | 250 mM mannitol | 65.8 | 1 |
| I* | | 150 mM arginine | 54.9 | 1 |
| J | | 250 mM proline | 65.2 | 1 |
| K* | 20 mM Tris pH 7.5 | 150 mM NaCl | 54.9 | 1 |
| L | | 250 mM sucrose | 64.3 | 1 |
| M | | 250 mM mannitol | 63.8 | 2 |
| N* | | 150 mM arginine | 54.6 | 3 |
| O | | 250 mM proline | 61.5 | 1 |
| P | | 50 mM acetate pH 5.0, 1% PPG | 56.6 | 1 |

*<50% recovery from buffer exchange

The melting temperature results, a measure of thermal stability, are in trend with the protein recoveries from buffer exchange, with sodium chloride and arginine as the worst excipients. Sucrose, mannitol and proline are clearly more favorable than sodium chloride and arginine. Histidine only slightly edges out acetate and Tris buffer formulations. Furthermore, the favorable excipients appear to exhibit similar thermal stability as their excipient-free equivalents, with melting temperatures of 63.4° C., 66.2° C. and 63.0° C. for Acetate pH 5.0, Histidine pH 6.0 and Tris pH 7.5, respectively.

$T_{agg}$ 266 nm results were collected and indicate that Formulations A, D, F, I, K and N show significant increases in scattering indicating aggregation, followed by a drop of intensity during further heating. This is due to the fact that very large protein aggregates precipitate and drop out of solution. SLS is only sensitive to species in solution, therefore upon precipitation the measured intensity drops. A closer evaluation of the SLS counts vs. Temperature plots show that formulations G, H and J light scattering remained below 12,000 counts in the evaluated temperature range (H and J were less than 10,000 counts in the temperature range). In comparison, the equivalent excipient-free buffer (Histidine 6.0) exhibited scattering of 10,000 counts at temperatures above 30° C. in the previous study, though sustained to <20,000 counts at the highest temperatures (FIG. 16). As such, another interpretation of the data was warranted to rank the formulations in terms of real aggregation events causing significant increases in light scattering (FIGS. 17 to 18). Overall, the ranking showed that formulations H and J (<10,000 counts in temperature range) were best, followed by formulations 0 and P having sustained SLS<10,000 counts up to 55° C., and followed by formulations B and G, which were comparable. It is also worth noting that the addition of Sucrose, Mannitol and Proline decreased scatter counts in comparison to their excipient-free buffer equivalent. For example, the addition of Mannitol decreased the maximum scatter counts from ~16,000 in Histidine pH 6.0 to ~5,000.

$T_{agg}$ 473 nm data was also collected. Compared to the $T_{agg}$ 266 nm data, similar issues were observed in the 473 nm SLS data in terms of observed counts. Therefore, formulations were ranked and summation of observations were:
- A, D, F, I, K and N "crash out" of solution, resulting in insoluble particles
- C, E, L and M exhibit comparable scatter ~1,000-1,500 above 25° C.
- B, G and J are comparable in counts at 95° C. (~1,000) and P scattering at 95° C. are comparable to C, E, L, M but later onsets It is of note, however, that in terms of SLS at 473 nm, the addition of excipient appeared to result in more scattering. Overall, Sucrose, Mannitol and Proline are more desirable excipients and Histidine pH 6 is a more favorable buffer. The least desirable excipients were Sodium Chloride and Arginine.

Dynamic Light Scattering

The DLS experiments were performed after centrifugation (10,000×g for 10 minutes) to get rid of any large particulates, and as triplicate analyses of neat samples using a DynaPro™ Plate Reader II instrument. Bracketing BSA preparations (2 mg/mL) were used to confirm system suitability. A total of 10 individual scans were performed at 25° C., with an acquisition time of 5 seconds for each sample. Data resulting from the software's autocorrelation function were manually curated for low cumulant fit errors, so those individual scans were marked and removed from the analysis. Since the Auto-Attenuation function was enabled to ensure optimal intensity count rates, the instrument automatically determined the Laser Power Percent for each measurement in real time. For high count rate measurements, Attenuation was set to 100% to protect the detector and minimize the Laser Power, resulting in unreliably low count results. As such, data acquired with Normalized Intensity (counts per second) of zero and Laser Power ≤20% were excluded. The resulting intensity distribution plots were compared to evaluate the effects of various formulation components on mean particle size by intensity (overall diameter), a global size distribution width parameter (overall percent polydispersity, or % Pd), the average peak diameter of the CTI-1601 monomer (Peak 1 diameter), and that peak's width parameter (Peak 1% Pd). It is important to note, however, that larger particles scatter more than smaller ones, so intensity distribution plots do not represent the particle size distribution in solution (i.e. ~30 nm diameter particles are not necessarily more abundant than ~5 nm diameter particles), but rather a graphical representation of determined particle size diameter populations. In addition, analysis typically cannot distinguish between monomeric and dimeric species because the instrument is only able to differentiate particles of 3-5 times larger radii. Percent polydispersity (overall or Peak 1) is a width parameter that reflects the heterogeneity detected in the intensity distribution plot, where % Pd<20% is indicative of a near-monodisperse solution and/or species conformation, and a "multimodal" result is generated if the value cannot be accurately determined due to high heterogeneity.

Considering protein recoveries ≤50% for formulations A, D, F, I, K and N, those sample's data was not included in data driven conclusions. Monomer peak diameter results are more weighted since overall diameter values are skewed by scattering of larger particles, and therefore do not always accurately reflect the particle size distribution. Poor cumulant fits (elevated baselines in the correlation function) are usually the result of number fluctuations—variations in the number of particles within the scattering volume during the course of a DLS measurement. These could be caused by the presence of large particles/aggregates.

Altogether, with the current DLS data, the more desirable formulations appeared to be Histidine pH 6.0 with monomer peak slightly smaller in Mannitol formulation. However, Mannitol results were comparable to excipient-free formulation, and monomer polydispersity data appeared to favor Proline.

DISCUSSION

Poor protein recoveries from buffer exchange of Sodium Chloride and Arginine formulations, irrespective of buffer type, indicate compatibility with the TAT-FXN fusion protein. Static light scattering data and melting temperatures confirmed this. DLS data is difficult to interpret due to limited data set. Histidine pH 6.0 data is more complete, except for data pertaining to the presence of the Sucrose excipient. Overall, Histidine pH 6.0 fared better and is recommended for further evaluation in the subsequent solubility study. Arginine and Sodium Chloride are not recommended for further evaluation.

Solubility Screening

Based upon data collected from baseline buffer and excipient screening studies, nine formulations with pH ranging from 6.0 to 7.5 in conjunction with three excipient types were evaluated for solubility. Additionally, a Histidine pH 7.0 formulation with and without Mannitol/Calcium Chloride was also evaluated.

All tested sample formulations were able achieve 130 mg/mL or higher concentrations with approximately 50% or higher recoveries. Notably, these high concentration samples all showed brown coloration. DLS results showed that all formulations exhibited high level of scattering which abrogated analysis. SEC results showed largely comparable % Main. SLS results ranked based on intensity, as a proxy for turbidity, showed that Histidine pH 6.0 is preferred. Based on the Sponsor's suggestion that Calcium Chloride is of formulaic importance, the surfactant screen was design to allow for evaluation of Sucrose, Mannitol, and Mannitol with 5 mM Calcium Chloride. These excipients were analyzed in Histidine pH 6.0 buffer with three surfactant types (PS80, PS20, and P188) and a no surfactant control. The study design also allowed for the inclusion of Tris/Mannitol at pH 7.5 with three surfactant types (PS 80, PS20, and PF-68) and a no surfactant control.

Surfactant Screening

The surfactants Polysorbate 80 (Fischer Sci. C/N P128329), Polysorbate 20 (Fischer Sci. C/N P128320) and Pluronic F-68 (Fischer Sci. C/N 24-040-032) were evaluated in combination with four buffer and excipient formulations to assess the stability/aggregation of the TAT-FXN fusion polypeptide during freeze-thaw and agitation stress. The target protein concentration for the study was 100 mg/mL. Protein samples were buffer exchanged and concentrated into surfactant-free buffer-excipient combinations using Amicon Ultra Centrifugal Filters (10 kDa NMWL Ultracel regenerated cellulose membrane, Millipore C/N UFC901096). To each pre-rinsed concentrator, 455 mg of the TAT-FXN fusion polypeptide was initially buffer exchanged into the appropriate buffer with multiple cycles of centrifugation and dilution, for a >500-fold exchange. Following the final buffer-exchange, the samples were concentrated to a volume of 2.5 mL and equivalent buffer/excipient formulations were pooled for a total of 4 different formulations. The protein concentration in the pooled samples was measured by UV-Visible spectroscopy ($\varepsilon$=1.647 ml/mg*cm). The pooled buffer/excipient formulations were normalized to 100 mg/mL using the appropriate buffer and split into four aliquots (~2.5 mL/aliquot). Surfactant was spiked into the appropriate samples at the specified concentration (spiking the equivalent volume of buffer-excipient in the surfactant-free formulations), and protein concentration in the samples was confirmed by UV-Visible spectroscopy. Content results are shown in Table 20; all content values ranged from 93 to 109 mg/mL.

Each sample was split into three aliquots (500-1000 μL per aliquot) and was protected from light for the duration of the study. One aliquot of each formulated sample was subjected to stress via freeze-thaw cycling (cryovial), one aliquot was subjected to agitation (glass vial), and one aliquot was stored at room temperature throughout the study to serve as a control (glass vial). For freezethaw cycling, the sample was frozen at −80° C. for at least 2 hours and then pulled and allowed to thaw to room temperature. This was repeated for a total of 5 cycles. The samples were stored at 2-8° C. until analysis. For agitation stress, the samples were agitated at 600 RPM at room temperature for 3 days. Final samples were stored at 2-8° C. until analysis. A total of ~7.3 g of material was consumed for this study, based on anticipated protein losses of 45%. As an initial assessment of solubility, turbidity was evaluated by measuring neat sample absorbance at 500 nm and visual appearance was evaluated. Physical stability of the protein in various buffers was evaluated by Native Static Light Scattering (SLS), Dynamic Light Scattering (DLS) and Size Exclusion Chromatography (SEC).

Visual Appearance

The samples formulated for surfactant screening were evaluated for appearance. It was determined that Freeze/thaw and agitation had no apparent impact on visual appearance. All samples appeared clear, slightly yellow in color, with no visible particulates.

Turbidity and Static Light Scattering

Samples subjected to agitation and freeze thaw stress conditions were evaluated neat for determination of turbidity using A500. The results of the evaluation indicate that no clear and consistent trend was observed, and the overall impact of surfactant to A500 appears to be neutral. The SLS results indicate that while the diluted sample set showed no clear trend associated with surfactant, the non-diluted samples showed a trend of slightly higher scattering in surfactant containing samples. However, given the small magnitude in scattering count differential, the dynamic range is not considered to be above the level of assay variability.

Size Exclusion Chromatography

All samples formulated with and without surfactant and subjected to agitation stress and freeze/thaw stress were evaluated for purity using SEC along with unstressed control samples (stored at 2-8° C.). The results of the evaluation for unstressed, agitation stress and freeze/thaw stress samples indicate that all samples showed a clear HMW and Main peak with no LMW detected. As a note, the data showed that PS80 and P F-68 consistently exhibited greater % HMW as compared to no surfactant or PS20 containing samples. Furthermore, in comparison between the no surfactant control and PS20 containing formulations, there appeared to be a slight benefit for inclusion of PS20 across no stress, agitation and freeze/thaw conditions.

Dynamic Light Scattering

Light scattering data was collected for centrifuged surfactant study samples. The samples subjected to agitation and freeze/thaw stress conditions were diluted in appropriate formulation buffer (without surfactant) to target 2 mg/mL and analyzed for size and polydispersity over three replicates. The results indicate that, based on Overall Diameter, Polysorbate surfactant appears to impart greater colloidal stability compared to no-surfactant and P F-68 containing samples. However, individual peak results do not show a clear trend to further re-affirm the trend seen in the Overall Diameter data.

DISCUSSION

While visual appearance, A500, SLS, and DLS results showed that surfactant generally had a neutral effect, SEC results indicated a positive impact associated with the inclusion of PS20. SEC data showed that PS20 containing samples showed a consistent, albeit small (~1 to 2%), decrease in % HMW in compared to other formulations across all stress conditions. Since the impact of PS20 was relatively small and limited to SEC, the inclusion of PS20 will be further evaluated.

Design of Experiment (DOE)

In order to determine the best performing formulation for the TAT-FXN fusion polypeptide of SEQ ID NO: 1, a DOE study was prepared to evaluate the effect of pH, excipient type, and PS20 on the TAT-FXN fusion polypeptide under short-term accelerated stability. The formulations used for the study are shown in Table 9 below.

TABLE 9

Formulations used for the DOE study

| ID | Buffer | Excipient | Surfactant | pH |
|---|---|---|---|---|
| A | 20 mM histidine | 250 mM sucrose | 0.05% PS20 | 5.5 |
| B | 20 mM histidine | 250 mM sucrose | 0.05% PS20 | 6.0 |
| C | 20 mM histidine | 250 mM sucrose | 0.05% PS20 | 6.0 |
| D | 20 mM histidine | 250 mM sucrose | 0.05% PS20 | 6.5 |
| E | 20 mM histidine | 250 mM sucrose | None | 5.5 |
| F | 20 mM histidine | 250 mM sucrose | None | 6.0 |
| G | 20 mM histidine | 250 mM sucrose | None | 6.0 |
| H | 20 mM histidine | 250 mM sucrose | None | 6.5 |
| I | 20 mM histidine | 250 mM mannitol | 0.05% PS20 | 5.5 |
| J | 20 mM histidine | 250 mM mannitol | 0.05% PS20 | 6.0 |
| K | 20 mM histidine | 250 mM mannitol | 0.05% PS20 | 6.0 |
| L | 20 mM histidine | 250 mM mannitol | 0.05% PS20 | 6.5 |
| M | 20 mM histidine | 250 mM mannitol | None | 5.5 |
| N | 20 mM histidine | 250 mM mannitol | None | 6.0 |
| O | 20 mM histidine | 250 mM mannitol | None | 6.0 |
| P | 20 mM histidine | 250 mM mannitol | None | 6.5 |
| Q | 20 mM histidine | 250 mM sucrose/ 5 mM CaCl$_2$ | 0.05% PS20 | 5.5 |
| R | 20 mM histidine | 250 mM sucrose/ 5 mM CaCl$_2$ | 0.05% PS20 | 6.0 |
| S | 20 mM histidine | 250 mM sucrose/ 5 mM CaCl$_2$ | 0.05% PS20 | 6.0 |
| T | 20 mM histidine | 250 mM sucrose/ 5 mM CaCl$_2$ | 0.05% PS20 | 6.5 |
| U | 20 mM histidine | 250 mM sucrose/ 5 mM CaCl$_2$ | None | 5.5 |
| V | 20 mM histidine | 250 mM sucrose/ 5 mM CaCl$_2$ | None | 6.0 |
| W | 20 mM histidine | 250 mM sucrose/ 5 mM CaCl$_2$ | None | 6.0 |
| X | 20 mM histidine | 250 mM sucrose/ 5 mM CaCl$_2$ | None | 6.5 |

TABLE 9-continued

Formulations used for the DOE study

| ID | Buffer | Excipient | Surfactant | pH |
|---|---|---|---|---|
| Y | 20 mM histidine | 250 mM mannitol/ 5 mM CaCl$_2$ | 0.05% PS20 | 5.5 |
| Z | 20 mM histidine | 250 mM mannitol/ 5 mM CaCl$_2$ | 0.05% PS20 | 6.0 |
| AA | 20 mM histidine | 250 mM mannitol/ 5 mM CaCl$_2$ | 0.05% PS20 | 6.0 |
| BB | 20 mM histidine | 250 mM mannitol/ 5 mM CaCl$_2$ | 0.05% PS20 | 6.5 |
| CC | 20 mM histidine | 250 mM mannitol/ 5 mM CaCl$_2$ | None | 5.5 |
| DD | 20 mM histidine | 250 mM mannitol/ 5 mM CaCl$_2$ | None | 6.0 |
| EE | 20 mM histidine | 250 mM mannitol/ 5 mM CaCl$_2$ | None | 6.0 |
| FF | 20 mM histidine | 250 mM mannitol/ 5 mM CaCl$_2$ | None | 6.5 |
| GG* | 20 mM histidine | 250 mM sucrose | None | 6.0 |
| HH* | 20 mM histidine | 250 mM sucrose | 0.05% PS20 | 6.0 |
| II* | 20 mM acetate | 250 mM sucrose | None | 5.5 |
| JJ** | 20 mM acetate | 250 mM sucrose | None | 5.5 |

*Contains 50 mg/mL TAT-FXN fusion polypeptide
**Contains 100 mg/mL TAT-FXN fusion polypeptide The DOE study involved evaluation of formulations at 100 mg/mL with Histidine at pH 5.5 to 6.5 along with two excipients (Sucrose and Mannitol) with and without Calcium Chloride. Furthermore, the inclusion of PS20 was included as a categorical factor. Lastly, four (4) off-DOE formulations were analyzed to: 1) aid in bridging with the current formulation containing 50 mM Acetate pH 5.0, 1% PPG, and 2) evaluate the effect of formulation at 50 mg/mL and 100 mg/mL.

Sample Preparation

Based on historical 60% protein recoveries, a total of 11.6 g of the TAT-FXN fusion polypeptide was used in this study to accommodate a 750 μL vial fill. Three separate lots of material were pooled, mixed and filtered to be used as starting material. The protein samples were buffer-exchanged into the buffer/excipient combinations. Samples were buffer-exchanged and concentrated using 10 kDa MWCO Amicon-15 concentrators (Millipore P/N UFC901096). The concentrators were pre-rinsed with the appropriate buffer exchange solution by adding 15 mL of solution to the filter, followed by centrifugation at ~3500×g for 8 minutes.

For each target 100 mg/mL formulation A-FF and JJ, a total of 325 mg of TAT-FXN fusion polypeptide was buffer exchanged using four (4) Amicon-15 concentrator units (81.25 mg per concentrator). Samples were centrifuged at 3500×g until a volume of ~5 mL was achieved.

For single DOE center-point formulations B, F, J, N, R, V, Z and DD, as well as Off-DOE formulation JJ, an additional 8.125 mg of material was added to each concentrator unit to account for the volume of sample necessary for viscosity testing. The buffer-exchange process continued with cycles of adding 10 mL of the buffer and then reducing the volume to ~5 mL by centrifugation, for a total of six (6) buffer exchanges and total dilution of ~700-fold. After the final buffer exchange cycle, single center-point formulation retentates were concentrated to ~0.55 mL per concentrator, while other retentates were concentrated to 0.5 mL per concentrator, then recovered from the concentrator units.

For each target 50 mg/mL Off-DOE formulation GG, HH and II, 178.75 mg of material was buffer exchanged using three (3) Amicon-15 concentrator units (59.58 mg per concentrator). Samples were centrifuged at 3500×g until a volume of ~3.5 mL was achieved. The buffer exchange process continued with cycles of adding 11.5 mL of the buffer and then reducing the volume to ~3.5 mL by centrifugation, for a total of four (4) buffer exchanges. In an additional final buffer exchange cycle, 4 mL of buffer was added to the retentate followed by centrifugation, for a final total dilution of ~700-fold. After the final buffer exchange cycle, retentates were concentrated to ~0.7 mL, then recovered from the concentrator units. Equivalent retentate samples were pooled, for a total of 15 samples, prior to protein content determination by UV-Visible spectroscopy (ε=1.647 ml/mg*cm). Protein content was measured again prior to normalizing to the target concentrations using the appropriate buffer. The recovered volumes of the samples were recorded to assess protein recovery. Retentate pools 1-13 were subsequently split into 2 aliquots. To one of the aliquots, Surfact-Amps 20 solution was added to 0.05% during the normalization step (calculated from the exact Surfact-Amps 20 concentration from the CofA). Following normalization, pooled formulations were split for a final total of 36 prepared formulations. Formulations were sterile filtered using Ultrafree-CL GV 0.22 μM sterile concentrators. To sterile filter, the entire volume of each formulation was transferred to a separate sterile filter, only opening the top part of the filter. The Ultrafree-CL units were spun at ~3200×g for 5 minutes until the entire solution passed through the 0.22 μM membrane. Following centrifugation, the filtering units were reopened inside the biosafety cabinet (BSC) at the time of vialing. Prior to use, the BSC was turned on for at least 15 minutes then sprayed down with 70% IPA. All items entering the were sprayed with 70% IPA prior to entering. A total of 2 vials per formulation were filled (0.75 mL fill volume) with the remainder residing in the sterile filter to use for T0 sample for testing, except for Appearance, performed using vialed material prior to staging. Appearance at T=0 was performed using one of the vials for each formulation prior to staging. One vial of each formulation was placed at 5° C. and one at 40° C./75% RH for the 3 Week incubation.

Appearance

Appearance results indicate that for T0 and 3W 5° C. samples, all formulations appeared to be clear, slightly yellow in color, and free of visible particulates. The 3W 40° C. samples also appeared to be clear, slightly yellow in color, and free of visible particulates. However, the stressed samples appeared to be highly viscous, with formulations Q, U and I appearing to have solidify.

Protein Content

Protein content results indicate that, while there are observable impact of storage and heat stress, generally, a visual trend is not apparent from the data.

Turbidity

Turbidity was evaluated via A550 for all samples, and results indicate that no visual trend was observed from the results.

pH

Sample pH was measured and results indicate that formulations demonstrated pH value within 0.2 pH unit of the target pH, with the exception of formulations H and JJ. Formulation H (100 mg/mL/Histidine/Sucrose/pH 6.5) exhibited pH of 6.9, and formulation JJ (100 mg/mL/Acetate/Sucrose/pH 5.5) exhibited pH value of 6.0. As this pH drift is unique to these samples and does not appear to be a global issue, the apparent pH will factor into the statistical data analysis.

Osmolality and Viscosity

Osmolality of all the center-point formulations were measured and results indicate that formulation osmolality appeared higher than anticipated with values ranging from 351 to 425 mOsm. The high osmolality results are likely due to the formulation buffer, as these buffers also exhibited osmolality in a comparable range (292 to 367 mOsm).

Viscosity measurement was performed at 3 different cone spindle speeds (10-100 range for Torque %). If apparent viscosity does not change as a function of shear rate, then the sample behaves in a Newtonian manner. If apparent viscosity changes as a function of shear rate, then the sample behaves in a Non-Newtonian manner. Pseudoplastic fluid displays a decreasing viscosity with increasing shear rate. Dilatant displays increasing viscosity with increasing shear rate. The results indicate that all samples showed Newtonian behavior. 50 mg/mL samples showed averaged viscosity results ranging from 1.8 to 2.9 cP. For 100 mg/mL samples, PS20 containing samples consistently showed lower cP values than those without PS20, and these values ranged from 14.7 to 28.5 cP. It should be noted that formulations with Calcium Chloride exhibited higher cp values than those without Calcium Chloride.

Dynamic Light Scattering

DLS results indicate the presence of aggregates as a result of the 40° C. heat stress. Notably, 3W/40° C. samples showed increase overall diameter size and multiple distinct species for the formulations tested. Though a differential in response can be noted, a general trend based on visual evaluation is not clear. Therefore, statistical analysis shall be leveraged for this data set in order to determine a significant trend.

Size Exclusion Chromatography

SEC results indicate that the % HMW results from 5 C and 40 C conditions both affirmed a pH dependency with optimal pH level at pH 5.5 and 6.5. Additionally, there appeared to be a preference for formulation without Calcium Chloride. Lastly, the presence of PS20 was generally neutral in effect with regards to % Main. The off DOE samples formulated at 50 mg/mL showed that there is a concentration dependent effect and 50 mg/mL showed lower % HMW.

Non-Reduced CGE

Non-Reduced (NR) CGE results indicate that inclusion of Calcium Chloride was not preferred as these formulations exhibited higher % HMW. Furthermore, inclusion of PS20 appears to be slightly preferred. These observations agree with SEC results, though a trend dependent on pH is not clearly discernable Reduced CGE Reduced (R) CGE data correlates directly with NR CGE results and is also in agreement with SEC data. The 5° C. % HMW result shows a pH dependency where pH 5.5 formulations showed lower % HMW. The role of PS20 was not clear and could be perceived as a neutral factor in these data. Similarly, Calcium Chloride was not noted to provide a clear benefit to the formulation.

Reversed Phase HPLC

RP HPLC results indicate a visual trend between pH and excipients was not clear and that the formulations are largely comparable. It is of note that the % main peak data (particularly 5° C. condition) shows further support that Calcium Chloride is not needed and may not be beneficial within the liquid formulation.

CEX

CEX results indicate that the differences between formulations are not particularly pronounced. Although there are differentials in terms of % Acidic, % Main and % Basic between the formulations, no clear visual trend was discerned.

Design of Experiment: Optimization Analysis

Analysis of DOE data was performed using Design-Expert 9 software. Buffer and excipient type for each formulation was entered as a categorical variable, while target pH was entered as a numeric variable. Analytical results were tested individually for statistical significance, where 5° C. and 3W 40° C. data collected were treated as separate responses. Only datasets deemed significant (p-value of fitting model <0.05), were used in the model for optimization analysis. In instances where multiple data sets or attributes demonstrated significance for the same terms, the data set with the highest R2 was included.

Overall, the model employed data from: 5° C. NR-CGE % HMW, 40° C. NR-CGE % HMW, 5° C. RCGE % Main, 40° C. R-CGE % Main, 5° C. SEC % Main, 40° C. SEC % Main, 5° C. RP Main, 40° C., RP Main, and 5° C. SLS 473 nm. The final output for the numerical optimization analyses are buffer/pH/excipient combinations and their associated desirability factors. Desirability is an objective function that ranges from 0 (no Desirability) to 1 (optimum goal). In the process used here, each of the responses was given an individual goal, where the numerical optimization finds a point that maximizes all goals using a single Desirability function. For an individual response, a goal was set to either maximize or minimize values within defined upper and lower limits based on the dynamic range of values obtained for DOE samples. In the DOE analysis, the optimized goal for a given response may be adjusted by altering the weight (0.1-10.0) and relative importance (+ to +++). In the present study, all response weights were left at 1.0, resulting in linear desirability over the indicated limit range. Response importance was varied over three profiles to test the robustness of the optimization process, i.e., evaluate the impact of different importance profiles on the final optimized formulation.

The results of the analysis indicate that, overall, inclusion of calcium chloride was not favorable and PS20 was beneficial for both Sucrose and Mannitol formulations. The differences between Sucrose and Mannitol was nuance and both appeared to be highly comparable based on the analytical data. Sucrose, however, was preferred over Mannitol due to its ability to be directly applied as a lyoformulation, whereas Mannitol would require to be couple with an additional excipient in lyoformulation. Formulation pH between 5.5 and 6.2 appears to be optimal. These trends are also confirmable from interpreting the data via tables and plots. Based on the data from the preformulation studies and the statistical analysis from the DOE, two candidate formulations were identified as follows:
1. 20 mM Histidine, 250 mM Sucrose, 0.05% PS20, pH 5.8
2. 20 mM Histidine, 250 mM Mannitol, 0.05% PS20, pH 5.8

Conclusions

The primary aim of the pre-formulation development studies presented in this report was to identify formulation components that would result in optimal physical, thermal, chemical and structural stability of the TAT-FXN fusion polypeptide of SEQ ID NO: 1 in liquid formulation under both stressed and non-stressed conditions. To this order, several buffer types, pH conditions, excipients, and surfactants were evaluated iteratively over the course of Baseline Buffer Evaluation, Excipient, Solubility, and Surfactant Screening studies, and a final Design of Experiment study. Based on these studies, the final formulation for initial clinical evaluation was established as 50 mg/mL CTI-1601 in 20 mM histidine, 250 mM sucrose, 0.05% polysorbate 20, pH 5.8. An alternative formulation was established as 50 mg/mL CTI-1601 in 20 mM histidine, 250 mM mannitol, 0.05% polysorbate 20, pH 5.8.

Example 2. Identification of the Lyophilized Formulation of the TAT-FXN Fusion Polypeptide The goal of this study was to perform a lyophilization study for TAT-FXN fusion polypeptide of SEQ ID NO: 1, given the molecule's general thermal instability. The primary aim of the lyophilization pre-formulation development studies was to identify formulations that would result in optimal chemical, physical and structural stability of lyophilized TAT-FXN fusion polypeptide under both stressed and non-stressed conditions.

The stability of lyophilized TAT-FXN fusion polypeptide of SEQ ID NO: 1 was evaluated using histidine pH 5.8 as base buffer, sucrose as the primary excipient and a panel of secondary excipients, including mannitol, commonly used in lyophilized therapeutic formulations, in addition to more unconventional reductants, such as ascorbic acid, glutathione and cysteine. Panel of formulations were chosen based on previous pre-formulation studies. The tested formulations are shown in Table 10 below.

TABLE 10

TAT-FXN Fusion Polypeptide Lyophilization Development Formulations

| Histidine Buffer | pH | Surfactant | Sucrose | Excipient 2 | Formulation |
|---|---|---|---|---|---|
| 20 mM | 5.8 | 0.05% PS20 | 250 mM | — | A |
|  |  |  | 50 mM | 220 mM mannitol | B |
| 40 mM |  |  | 220 mM | — | C |
|  |  |  |  | 40 mM ascorbic acid | D |
| 20 mM | 5.8 |  |  | 40 mM glutathione | E |
|  |  |  |  | 40 mM cysteine | F |
| 40 mM |  | 0.05% PS20 | 60 mM | 200 mM mannitol | G |
|  |  |  | 190 mM | 40 mM ascorbic acid | H |
|  |  |  |  | 40 mM glutathione | I |
|  |  |  |  | 40 mM cysteine | J |
|  |  |  |  | 0.5% PG | K |
| 20 mM |  |  | 250 mM | — | L |

Prior to initiating any lyophilization activity, ~1.0 mL of TAT-FXN fusion polypeptide formulated in each of the twelve (12) formulations shown in Table 10, was prepared through buffer-exchange process. After the dialysis process, measured protein concentration was slightly lower than the target 50 mg/mL, thus samples were normalized to 40 mg/mL. To bridge any potential impact caused by the difference in concentration, one (1) mL aliquot of each formulated sample was removed prior to normalization. This sample was vialed and lyophilized as the higher concentration representative, referred to as pre-norm lyo and was tested at T0. During final normalization to 40 mg/mL, surfactant (PS20) was added to all formulations to 0.050% using a 10% (w/v) stock solution. Following buffer-exchange and normalization, the formulations were sterile filtered using 0.2 μm sterile filter flasks.

Glass-Transition Temperature (Tg') Determination

Glass transition temperature of freeze-concentrated solutions (Tg') was determined using differential scanning calorimetry. Tg' as well as the crystallization behavior of excipients are important physicochemical characteristics which guide the cycle development in freeze-drying, specifically the determination of the primary drying temperature, which is generally set to the realm or below that of the Tg'. The transition temperatures ranged from −36.9° C. to −27.2° C., which is within expectation for sucrose and mannitol containing formulations. Out of the twelve Tg' evaluated formulations, the first 6 (Formulations A-F shown in Table 10) were chosen for the lyophilization development study.

Lyophilization and Short-Term Stability

The lyophilization cycle consisted of an initial annealing step, where the temperature was cycled from −50° C. to −20° C. for a few hours to allow for complete crystallization of the mannitol containing formulation. Subsequent to the annealing step, primary drying was initiated by setting the pressure at 100 mTorr and ramping the shelf temperature to −25° C., cycle was held at primary drying for 3184 min (~53 hrs). Once primary drying was completed, a secondary drying to remove any remaining moisture was performed by ramping the temperature to 30° C. and holding it for 600 min (10 hrs). The total lyophilization cycle duration was 4989 min (~3.5 days). At the completion of the cycle, vials were backfilled with nitrogen at a partial pressure of about 570 Torrs, stoppered and appropriately sealed.

Appearance

All lyophilized cakes, through the entire short-term stability, showed intact structures of white color, except for formulation D, that color was observed to be reddish-brown. This reddish-brown coloration is most likely caused by the ascorbic acid, added as a reductant to the formulation. After reconstitution and frozen control liquid appearance was observed to be clear and free of visible particulates for all sample types, time points and conditions. However, color changed slightly, with the exception of the reddish color for all formulation D samples, remaining T0 samples were observed to be colorless, while the 2 and 4-week timepoint conditions were observed to be slightly yellow. Overall, no major impact on sample appearance was observed.

Residual Moisture

Overall, results for residual moisture content ranged from 0.3%-1.6%, being the higher moisture values associated with the 4-week time point samples stored at 40° C. Formulation D exhibited the highest overall moisture content, while formulations A and C, overall, exhibited lower moisture cakes.

Reconstitution Time

The material in each vial dissolved completely leaving no visible residue or undissolved matter within a period of 68 seconds.

pH

The pH of all samples was determined to be 5.7±0.1.

A280 Content

Measured A280 content values ranged from 36.5 mg/mL to 49.9 mg/mL across all time points and conditions.

Turbidity

Turbidity at 320 nm measured for all samples across all time points and conditions indicate slightly elevated turbidity for formulation F, T0 and −75° C. samples. Formulations A and B exhibited the lowest turbidity values at 2 and 4-weeks' time points, independent of the condition.

Osmolality

Osmolality was measured for all samples and the results ranged from 278-366 mOsm/kg across all time points and conditions.

Ellman's (Free Thiol)

Reduced sulfhydryl groups within TAT-FXN fusion polypeptide were quantified using Ellman's reagent. Formulations A and B exhibited ~1 molar ratio of free thiol to the TAT-FXN fusion polypeptide across all time points and conditions. Formulation C, T0 liquid control, 4-week frozen control and T0 reconstituted exhibited the molar ratio of free thiol to TAT-FXN fusion polypeptide to be <0.5, suggesting that, in this formulation, and under these conditions, TAT-FXN fusion polypeptide may be slightly oxidized. Across all time points and conditions, Formulation D showed low ratios of free thiol to TAT-FXN fusion polypeptide, indicating that the presence of ascorbic acid did not seem to provide an overall reduced environment and the majority of the protein is in its oxidized state.

Formulations E and F were not evaluated for free thiol due to the presence of the thiol containing compounds, cysteine and glutathione. Free thiol results are in line with the results obtained for IEC.

Micro Flow Imaging (MFI)

Particle size distribution and morphology was evaluated by MFI. Total particle counts were generally within acceptable limits for all formulations. Morphological filters indicate the presence of silicone droplets and gas/air bubbles, which have contributed to slightly higher count numbers at the ≥2 and ≥5 size ranges. However, morphological filter applied to select for proteinaceous particulates shows that counts for lyophilized samples are lower than liquid and frozen control samples, indicating lack of larger size particulates.

Size Exclusion Chromatography (SE-UPLC)

Main peak purity and higher order aggregates of TAT-FXN fusion polypeptide were evaluated by SEC. Lyophilized TAT-FXN fusion polypeptide and controls, in Formulations A, B, C, E and F exhibited relative main peak purity >97%, across all time points and conditions. Formulation D on the other hand, across all time points and conditions, exhibited relative area of higher molecular weight species >14%. Results observed for SEC correlates with RP-HPLC results.

Ion Exchange Chromatography (IE-HPLC)

Charge heterogeneity and chemical modifications, such as oxidation, were evaluated through cation exchange chromatography. Formulations A, B and C exhibited the highest total relative main peak area of the six formulations, while formulation D exhibited the lowest. Across all formulations and conditions, formulation A exhibited the highest percent reduced main peak.

Reverse Phase Chromatography (RP-HPLC)

TAT-FXN fusion polypeptide purity was evaluated through reverse phase chromatography. Formulations A and B showed the highest main peak purity across all formulations and conditions.

Conclusions

The goal of this study was to perform a lyophilization study for TAT-FXN fusion polypeptide of SEQ ID NO: 1, given the molecule's general thermal instability. The primary aim of the lyophilization pre-formulation development studies was to identify formulations that would result in optimal chemical, physical and structural stability of lyophilized TAT-FXN fusion polypeptide under both stressed and non-stressed conditions. This study employed buffer/excipient combinations identified during liquid formulation screening that are amenable to lyophilization (histidine buffer with sucrose and/or mannitol), as well as presence of additives that can promote an overall reduced environment for the protein, such as ascorbic acid, cysteine and glutathione. For lyophilization cycle development, a common conservative lyophilization cycle was performed for TAT-FXN fusion polypeptide formulated into the six (6) different buffers. The target protein concentration for all lyophilized formulations was 40.0 mg/mL. Based on results for the lyophilized pre-formulation studies, 20 mM histidine, 250 mM sucrose, 0.05% PS20, pH 5.8 was selected as the most suitable formulation for the TAT-FXN fusion polypeptide. This formulation confers maximal chemical, physical, and conformation stability to the TAT-FXN fusion polypeptide at the target concentration of 40 mg/mL when compared across all the evaluated lyophilized drug substance formulations and it is also the current liquid formulation.

Example 3. Stability Data for a Liquid Pharmaceutical Composition of the TAT-FXN Fusion Protein The goal of this study was to determine stability of a pharmaceutical composition of the disclosure. The pharmaceutical composition contained TAT-FXN fusion polypeptide of SEQ ID NO: 1 at a concentration of 50 mg/mL in 20 mM histidine, 250 mM sucrose, 0.05% polysorbate 20 at pH of 5.8. The pharmaceutical composition was stored in liquid form in 2 mL glass vials (1.2 mL fill) at the temperature of ≤−60° C. for up to 24 months, and the stability of the formulation was evaluated at different time points. The results of the stability evaluation are presented in the Table 11 below.

TABLE 11

Results of Stability Study at ≤−60° C.

| Test | Acceptance Criterion | Time (months) | | | | | | | | |
|---|---|---|---|---|---|---|---|---|---|---|
| | | 0 | 1 | 3 | 6 | 9 | 12 | 18 | 24 | 36 |
| Appearance | Clear to slightly opalescent colorless to slightly yellow liquid, generally free of visible particulates | Clear, colorless liquid, free of visible particulates | Slightly yellow, clear liquid, free of visible particulates | Clear, colorless liquid, free of visible particulates | Clear, colorless liquid, free of visible particulates | Clear, colorless liquid, free of visible particulates | Clear, colorless liquid, free of visible particulates | Clear, slightly yellow liquid, free of visible particulates | Clear, slightly yellow liquid, free of visible particulates | TBD |
| pH | 5.4-6.2 | 6.1 | 6.1 | 5.9 | 5.8 | 5.9 | 5.8 | 6.1 | 5.9 | TBD |
| A280 (mg/mL) | 45-55 mg/mL | 51 | 51 | 50 | 51 | 53 | 51 | 52 | 51 | TBD |

TABLE 11-continued

Results of Stability Study at ≤ −60° C.

| Test | Acceptance Criterion | Time (months) | | | | | | | | |
|---|---|---|---|---|---|---|---|---|---|---|
| | | 0 | 1 | 3 | 6 | 9 | 12 | 18 | 24 | 36 |
| RP-HPLC (%) | ≥95.0% Main | 97.3 | 97.8 | 97.7 | 97.9 | 98.2 | 97.3 | 97.6 | 97.7 | TBD |
| SE-UPLC (%) | ≥95.0% Main | 97.7 | 98.8 | 99.0 | 99.3 | 98.2 | 99.1 | 99.2 | 98.9 | TBD |
| HMW (%) | ≤4% | 1 | 1 | 1 | 1 | 2 | 1 | 1 | 1 | |
| CE-SDS (%) Reduced | ≥95.0% Main Peak | 97.5 | 98.0 | 97.8 | 99.0 | 99.0 | 98.9 | 98.4 | 98.7 | TBD |
| Non-reduced | ≥92.0% Main Peak | 97.1 | 98.6 | 97.2 | 96.0 | 97.1 | 98.9 | 98.8 | 95.6 | |
| Potency (%) | % Specific Activity 60%-140% | 89 | 90 | 85 | 87 | 99 | 100 | 89 | 73 | TBD |
| Endotoxin (EU/mg) | ≤0.4 EU/mg | <0.4 | NT* | NT | NT | NT | <0.4 | NT | <0.4 | TBD |
| Sterility | No Growth | No Growth | NT | NT | NT | NT | NT | NT | NT | TBD |
| Particulate Matter | ≥10 μm: NMT 6000 Particles/Container | 302 | NT | NT | NT | NT | 3 | NT | 75 | |
| | ≥25 μm: NMT 600 Particles/Container | 17 | | | | | 1 | | 1 | |
| CCIT | No ingress | NT | NT | NT | NT | NT | No ingress | NT | NT | TBD |

*NT = not tested.
*TBD = to be determined.

The results of the stability study indicate that the tested composition is stable at the temperature of ≤−60° C. for at least 24 months.

A similar study was carried out to determine stability of the pharmaceutical composition containing TAT-FXN fusion polypeptide of SEQ ID NO: 1 at a concentration of 50 mg/mL in 20 mM histidine, 250 mM sucrose, 0.05% polysorbate 20 at pH of 5.8 at −20° C.±5° C. The results of this study for the time point of 24 months are presented in Table 12 below.

TABLE 12

Results of Stability Study at −20° C. ± 5° C.

| Test | Acceptance Criterion | Time (months) |
|---|---|---|
| Appearance | Clear to slightly opalescent colorless to slightly yellow liquid, generally free of visible particulates | Clear, slightly yellow liquid, free of visible particulates |
| pH | 5.4-6.2 | 5.9 |
| A280 (mg/mL) | 45-55 mg/mL | 51 |
| RP-HPLC (%) | ≥95.0% Main | 97.5 |

TABLE 12-continued

Results of Stability Study at −20° C. ± 5° C.

| Test | Acceptance Criterion | Time (months) |
|---|---|---|
| SE-UPLC (%) | ≥95.0% Main | 98.9 |
| HMW (%) | ≤4% | 1 |
| CE-SDS (%) | ≥95.0% Main Peak | 98.4 |
| Reduced Non-reduced | ≥92.0% Main Peak | 96.4 |
| Potency (%) | % Specific Activity 60%-140% | 86 |
| Endotoxin (EU/mg) | ≤0.4 EU/mg | ≤0.4 EU/mg |
| Sterility | No Growth | NT |
| Particulate Matter | ≥10 μm: NMT 6000 Particles/Container | 14 |
| | ≥25 μm: NMT 600 Particles/Container | 0 |
| CCIT | No ingress | NT |

The results of the stability study indicate that the tested composition is stable at the temperature of −20° C.±5° C. for at least 24 months.

What is claimed is:

1. A pharmaceutical composition comprising a fusion polypeptide, a buffer, a pharmaceutically acceptable excipient and a pharmaceutically acceptable carrier, wherein:
   said fusion polypeptide comprises an amino acid sequence with at least about 90% sequence identity to the amino acid sequence of SEQ ID NO: 1;
   said fusion polypeptide is present in said pharmaceutical composition at a concentration of about 20 mg/mL to about 75 mg/mL;
   said pharmaceutically acceptable excipient is a sugar selected from the group consisting of sucrose and mannitol;
   said buffer is histidine;
   wherein pH of the pharmaceutical composition is between about 5.0 and about 7.0; and
   wherein said pharmaceutical composition is stable for at least 12 months when stored at a temperature of about −60° C. or lower.

2. The pharmaceutical composition of claim 1, wherein said fusion polypeptide is present in said pharmaceutical composition at a concentration of about 50 mg/mL.

3. The pharmaceutical composition of claim 1, wherein the sugar is present in said pharmaceutical composition at a concentration of about 1 mM to about 500 mM.

4. The pharmaceutical composition of claim 1, wherein the sugar is present in said pharmaceutical composition at a concentration of about 250 mM.

5. The pharmaceutical composition of claim 1, wherein said buffer is present in said pharmaceutical composition at a concentration of between about 5 mM to about 500 mM.

6. The pharmaceutical composition of claim 5, wherein said buffer is present in said pharmaceutical composition at a concentration of about 20 mM.

7. The pharmaceutical composition of claim 1, wherein the pH of the pharmaceutical composition is about 5.8.

8. The pharmaceutical composition of claim 1, further comprising a surfactant.

9. The pharmaceutical composition of claim 8, wherein said surfactant is a non-ionic surfactant.

10. The pharmaceutical composition of claim 8, wherein said surfactant is selected from the group consisting of polyoxyethylene glycol octylphenol ethers, polyoxyethylene glycol alkylphenol ethers (Nonoxynol-9), polyoxyethylene glycol sorbitan alkyl esters (Polysorbate), sorbitan alkyl esters (Span), and block copolymers of polyethylene glycol and polypropylene glycol (Poloxamers).

11. The pharmaceutical composition of claim 10, wherein said surfactant is polyethylene glycol sorbitan monolaurate (Polysorbate 20).

12. The pharmaceutical composition of claim 11, wherein said surfactant is present is said pharmaceutical composition at a concentration of about 0.05% w/v.

13. The pharmaceutical composition of claim 8, wherein said surfactant is present in said pharmaceutical composition at a concentration of about 0.0001% w/v to about 1% w/v.

14. The pharmaceutical composition of claim 1, wherein said pharmaceutically acceptable carrier is water.

15. The pharmaceutical composition of claim 1, wherein said pharmaceutical composition is amenable to lyophilization.

16. The pharmaceutical composition of claim 1, wherein said pharmaceutical composition is suitable for injection.

17. The pharmaceutical composition of claim 1, wherein said pharmaceutical composition is suitable for a subcutaneous injection.

18. The pharmaceutical composition of claim 1, wherein said pharmaceutical composition is in liquid form.

19. A method of treating a disease, said method comprising administering to a subject in need thereof the pharmaceutical composition of claim 1.

20. The method of claim 19, wherein said disease is Friedreich's Ataxia (FRDA).

21. The method of claim 19, wherein said disease is an FRDA-associated disease.

22. The pharmaceutical composition of claim 1, wherein said fusion polypeptide comprises the amino acid sequence of SEQ ID NO: 1.

23. The pharmaceutical composition of claim 1, wherein said fusion polypeptide consists of the amino acid sequence of SEQ ID NO: 1.

24. A pharmaceutical composition comprising a fusion polypeptide, a pharmaceutically acceptable excipient, a pharmaceutically acceptable carrier, a buffer and a surfactant, wherein:
   said fusion polypeptide comprises an amino acid sequence with at least about 90% sequence identity to the amino acid sequence of SEQ ID NO: 1;
   said fusion polypeptide is present in said pharmaceutical composition at a concentration of about 20 mg/mL to about 75 mg/mL;
   said pharmaceutically acceptable excipient is a sugar selected from the group consisting of sucrose and mannitol, wherein said sugar is present in said pharmaceutical composition at a concentration of about 100 mM to about 300 mM;
   said buffer is histidine, wherein said buffer is present in said pharmaceutical composition at a concentration of about 5 mM to about 50 mM;
   wherein pH of the pharmaceutical composition is between about 5.0 and about 7.0; and
   wherein said pharmaceutical composition is stable when stored at a temperature of about −60° C. or lower for at least 12 months.

25. The pharmaceutical composition of claim 24, wherein said pharmaceutically acceptable excipient is sucrose.

26. The pharmaceutical composition of claim 24, wherein said surfactant is polyethylene glycol sorbitan monolaurate (Polysorbate 20).

27. The pharmaceutical composition of claim 24, wherein said pharmaceutically acceptable carrier is water.

28. The pharmaceutical composition of claim 24, wherein said pharmaceutical composition is in liquid form.

29. The pharmaceutical composition of claim 24, wherein said fusion polypeptide comprises the amino acid sequence of SEQ ID NO: 1.

30. The pharmaceutical composition of claim 24, wherein said fusion polypeptide consists of the amino acid sequence of SEQ ID NO: 1.

31. The pharmaceutical composition of claim 24, wherein the pH of the pharmaceutical composition is about 5.8.

32. The pharmaceutical composition of claim 24, wherein said fusion polypeptide is present in said pharmaceutical composition at a concentration of about 50 mg/mL.

33. A method of treating a disease, said method comprising administering to a subject in need thereof the pharmaceutical composition of claim 24.

34. The method of claim 33, wherein said disease is Friedreich's Ataxia (FRDA).

35. The method of claim 33, wherein said disease is an FRDA-associated disease.

36. A pharmaceutical composition comprising a fusion polypeptide, sucrose, histidine, a polyethylene glycol sorbitan monolaurate (Polysorbate 20), and water, wherein:
    said fusion polypeptide comprises an amino acid sequence with at least about 90% sequence identity to the amino acid sequence of SEQ ID NO: 1;
    wherein said fusion polypeptide is present in said pharmaceutical composition at a concentration of about 20 mg/mL to about 75 mg/mL;
    wherein said sucrose is present in said pharmaceutical composition at a concentration of about 100 mM to about 300 mM;
    wherein said histidine is present in said pharmaceutical composition at a concentration of about 5 mM to about 50 mM;
    wherein pH of the pharmaceutical composition is between about 5.0 and about 7.0; and
    wherein said pharmaceutical composition is stable when stored at a temperature of about −60° C. or lower for at least 12 months.

37. The pharmaceutical composition of claim 36, wherein said pharmaceutical composition is in liquid form.

38. The pharmaceutical composition of claim 36, wherein said fusion polypeptide comprises the amino acid sequence of SEQ ID NO: 1.

39. The pharmaceutical composition of claim 36, wherein said fusion polypeptide consists of the amino acid sequence of SEQ ID NO: 1.

40. The pharmaceutical composition of claim 36, wherein the pH of the pharmaceutical composition is about 5.8.

41. The pharmaceutical composition of claim 36, wherein said fusion polypeptide is present in said pharmaceutical composition at a concentration of about 50 mg/mL.

42. A method of treating a disease, said method comprising administering to a subject in need thereof the pharmaceutical composition of claim 36.

43. The method of claim 42, wherein said disease is Friedreich's Ataxia (FRDA).

44. The method of claim 42, wherein said disease is an FRDA-associated disease.

45. A pharmaceutical composition comprising a fusion polypeptide, 250 mM sucrose, 20 mM histidine, 0.05% w/v polyethylene glycol sorbitan monolaurate (Polysorbate 20), and water, wherein
    said fusion polypeptide comprises an amino acid sequence with at least about 90% sequence identity to the amino acid sequence of SEQ ID NO: 1;
    wherein said fusion polypeptide is present in said pharmaceutical composition at a concentration of about 20 mg/mL to about 75 mg/mL;
    wherein pH of the pharmaceutical composition is between about 5.0 and about 7.0; and
    wherein said pharmaceutical composition is stable when stored at a temperature of about −60° C. or lower for at least 12 months.

46. The pharmaceutical composition of claim 45, wherein said pharmaceutical composition is in liquid form.

47. The pharmaceutical composition of claim 45, wherein said fusion polypeptide comprises the amino acid sequence of SEQ ID NO: 1.

48. The pharmaceutical composition of claim 45, wherein said fusion polypeptide consists of the amino acid sequence of SEQ ID NO: 1.

49. The pharmaceutical composition of claim 45, wherein the pH of the pharmaceutical composition is about 5.8.

50. A method of treating a disease, said method comprising administering to a subject in need thereof the pharmaceutical composition of claim 45.

51. The method of claim 50, wherein said disease is Friedreich's Ataxia (FRDA).

52. The method of claim 50, wherein said disease is an FRDA-associated disease.

53. A pharmaceutical composition comprising a fusion polypeptide, 250 mM sucrose, 20 mM histidine, 0.05% w/v polyethylene glycol sorbitan monolaurate (Polysorbate 20), and water, wherein
    said fusion polypeptide comprises the amino acid sequence of SEQ ID NO: 1;
    wherein said fusion polypeptide is present in said pharmaceutical composition at a concentration of about 50 mg/mL;
    wherein pH of said pharmaceutical composition is about 5.8; and
    wherein said pharmaceutical composition is stable when stored at a temperature of about −60° C. or lower for at least 12 months.

54. A method of treating a disease, said method comprising administering to a subject in need thereof the pharmaceutical composition of claim 53.

55. The method of claim 54, wherein said disease is Friedreich's Ataxia (FRDA).

56. The method of claim 54, wherein said disease is an FRDA-associated disease.

* * * * *

SEQUENCE LISTING

```
<160> NUMBER OF SEQ ID NOS: 10

<210> SEQ ID NO 1
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Tyr Gly Arg Lys Lys Arg Arg Gln Arg Arg Gly Gly Met Trp
1               5                   10                  15

Thr Leu Gly Arg Arg Ala Val Ala Gly Leu Leu Ala Ser Pro Ser Pro
            20                  25                  30
```

```
Ala Gln Ala Gln Thr Leu Thr Arg Val Pro Arg Pro Ala Glu Leu Ala
         35                  40                  45

Pro Leu Cys Gly Arg Arg Gly Leu Arg Thr Asp Ile Asp Ala Thr Cys
 50                  55                  60

Thr Pro Arg Arg Ala Ser Ser Asn Gln Arg Gly Leu Asn Gln Ile Trp
 65                  70                  75                  80

Asn Val Lys Lys Gln Ser Val Tyr Leu Met Asn Leu Arg Lys Ser Gly
                 85                  90                  95

Thr Leu Gly His Pro Gly Ser Leu Asp Glu Thr Thr Tyr Glu Arg Leu
                100                 105                 110

Ala Glu Glu Thr Leu Asp Ser Leu Ala Glu Phe Phe Glu Asp Leu Ala
        115                 120                 125

Asp Lys Pro Tyr Thr Phe Glu Asp Tyr Asp Val Ser Phe Gly Ser Gly
    130                 135                 140

Val Leu Thr Val Lys Leu Gly Gly Asp Leu Gly Thr Tyr Val Ile Asn
145                 150                 155                 160

Lys Gln Thr Pro Asn Lys Gln Ile Trp Leu Ser Ser Pro Ser Ser Gly
                165                 170                 175

Pro Lys Arg Tyr Asp Trp Thr Gly Lys Asn Trp Val Tyr Ser His Asp
                180                 185                 190

Gly Val Ser Leu His Glu Leu Leu Ala Ala Glu Leu Thr Lys Ala Leu
            195                 200                 205

Lys Thr Lys Leu Asp Leu Ser Ser Leu Ala Tyr Ser Gly Lys Asp Ala
        210                 215                 220

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Tyr Gly Arg Lys Lys Arg Arg Gln Arg Arg Arg
1               5                   10

<210> SEQ ID NO 3
<211> LENGTH: 80
<212> TYPE: PRT
<213> ORGANISM: Homo sapiens

<400> SEQUENCE: 3

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
                20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
        50                  55                  60

Ile Trp Asn Val Lys Lys Gln Ser Val Tyr Leu Met Asn Leu Arg Lys
65                  70                  75                  80

<210> SEQ ID NO 4
<211> LENGTH: 210
<212> TYPE: PRT
<213> ORGANISM: Homo sapiens
```

```
<400> SEQUENCE: 4

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Gly Leu Arg Thr Asp Ile Asp Ala
            35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
                100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
                180                 185                 190

Ala Leu Lys Thr Lys Leu Asp Leu Ser Ser Leu Ala Tyr Ser Gly Lys
            195                 200                 205

Asp Ala
    210

<210> SEQ ID NO 5
<211> LENGTH: 130
<212> TYPE: PRT
<213> ORGANISM: Homo sapiens

<400> SEQUENCE: 5

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
            20                  25                  30

Leu Ala Asp Lys Pro Tyr Thr Phe Glu Asp Tyr Asp Val Ser Phe Gly
        35                  40                  45

Ser Gly Val Leu Thr Val Lys Leu Gly Gly Asp Leu Gly Thr Tyr Val
    50                  55                  60

Ile Asn Lys Gln Thr Pro Asn Lys Gln Ile Trp Leu Ser Ser Pro Ser
65                  70                  75                  80

Ser Gly Pro Lys Arg Tyr Asp Trp Thr Gly Lys Asn Trp Val Tyr Ser
                85                  90                  95

His Asp Gly Val Ser Leu His Glu Leu Leu Ala Ala Glu Leu Thr Lys
                100                 105                 110

Ala Leu Lys Thr Lys Leu Asp Leu Ser Ser Leu Ala Tyr Ser Gly Lys
            115                 120                 125

Asp Ala
    130
```

<210> SEQ ID NO 6
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
catatgtatg gtagaaagaa acgtcgtcaa cgtcgtcgtg gtggtatgtg gaccttgggc    60
cgtcgcgcgg ttgcgggcct gctggcgagc ccaagcccgg cacaggcgca gaccctgacg   120
cgcgttccgc gtccggcgga attggccccg ttgtgcggtc gccgtggtct gcgcacggat   180
atcgacgcta cctgtacgcc gcgtcgcgcg agcagcaatc agcgtggcct gaatcaaatt   240
tggaacgtca agaaacaatc tgtttacctg atgaatctgc gcaagagcgg tacgttgggt   300
cacccgggca gcctggacga gactacctat gagcgcctgg ctgaggaaac gctggacagc   360
ctggccgaat ttttcgaaga tctcgcagat aagccgtaca cgtttgagga ttatgacgtg   420
agcttcggca gcggcgtctt aaccgtgaaa ctgggtggtg acctgggcac ctacgtgatc   480
aataagcaaa ccccgaacaa acagatttgg ctgagctcgc cgagctctgg ccctaagcgt   540
tacgattgga ccggtaagaa ctgggtgtat tcccacgacg gtgtcagcct gcatgaactg   600
ctggcggcag agctgaccaa agcgctgaaa actaaactgg atctgagctc cctggcctac   660
agcggtaaag acgcataact cgag                                          684
```

<210> SEQ ID NO 7
<211> LENGTH: 11
<212> TYPE: PRT
<213> ORGANISM: Human immunodeficiency virus 1

<400> SEQUENCE: 7

Tyr Gly Arg Lys Lys Arg Arg Gln Arg Arg Arg
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Gly Gly Gly Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser
1               5

<210> SEQ ID NO 10
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 10

Gly Ser Ala Gly Ser Ala Ala Gly Ser Gly Glu Phe
1               5                   10
```